(12) United States Patent
Rizzo et al.

(10) Patent No.: US 11,266,183 B2
(45) Date of Patent: Mar. 8, 2022

(54) SYSTEMS AND METHOD FOR COMPRESSION CONTROL IN A WEARABLE COMPRESSION DEVICE

(71) Applicant: RECOVERY FORCE, LLC, Fishers, IN (US)

(72) Inventors: Vince Rizzo, Westfield, IN (US); Jeffrey Schwegman, Indianapolis, IN (US)

(73) Assignee: RECOVERY FORCE, LLC, Fishers, IN (US)

(*) Notice: Subject to any disclaimer, the term of this patent is extended or adjusted under 35 U.S.C. 154(b) by 711 days.

(21) Appl. No.: 15/917,122

(22) Filed: Mar. 9, 2018

(65) Prior Publication Data

US 2019/0274372 A1    Sep. 12, 2019

(51) Int. Cl.
| | |
|---|---|
| A61F 13/08 | (2006.01) |
| A61H 11/00 | (2006.01) |
| A61H 1/00 | (2006.01) |
| A41D 1/00 | (2018.01) |

(52) U.S. Cl.
CPC .............. *A41D 1/002* (2013.01); *A61F 13/08* (2013.01); *A61H 2201/0103* (2013.01); *A61H 2201/0192* (2013.01); *A61H 2201/5007* (2013.01); *A61H 2201/5071* (2013.01); *A61H 2201/5097* (2013.01); *A61H 2209/00* (2013.01)

(58) Field of Classification Search
None
See application file for complete search history.

(56) References Cited

U.S. PATENT DOCUMENTS

| | | | | |
|---|---|---|---|---|
| 5,669,872 | A | * | 9/1997 | Fox ...................... A61H 9/0078 128/898 |
| 5,968,073 | A | * | 10/1999 | Jacobs ................... A61B 34/74 601/152 |
| 6,174,486 | B1 | | 1/2001 | Jin-Ya et al. |
| 2015/0313608 | A1 | | 11/2015 | Baudenbacher et al. |
| 2016/0074234 | A1 | * | 3/2016 | Abichandani .......... G05B 15/02 601/84 |

(Continued)

FOREIGN PATENT DOCUMENTS

WO    WO 2017/189926 A1    11/2017

OTHER PUBLICATIONS

International Search Report and Written Opinion dated May 13, 2019 in PCT/US2019/020894, 13 pages.

*Primary Examiner* — Bradley H Philips
*Assistant Examiner* — Savannah L Gabriel
(74) *Attorney, Agent, or Firm* — Maginot, Moore & Beck, LLP

(57) ABSTRACT

An active compression device includes a textile wrap configured to be secured around a waist of a user. Additionally, the active compression device includes a controller assembly disposed within the textile wrap, wherein the controller assembly includes one or more shape memory wires configured to apply compression to the user's back in response to actuation of the one or more shape memory wires. The controller assembly also includes processing circuitry configured to receive a selection of a predetermined compression profile, and in response to receiving the selection of the predetermined compression profile, activate a predetermined pattern of compressions corresponding to the selected predetermined compression profile.

20 Claims, 12 Drawing Sheets

(56) References Cited

U.S. PATENT DOCUMENTS

| | | | | |
|---|---|---|---|---|
| 2016/0175179 A1* | 6/2016 | Pamplin | ................. | A61H 7/001 |
| | | | | 601/84 |
| 2016/0331620 A1* | 11/2016 | Kazanchyan | ........ | A61N 1/3603 |
| 2016/0374886 A1* | 12/2016 | Wyatt | .................... | A61H 7/007 |
| | | | | 601/18 |
| 2017/0196502 A1* | 7/2017 | Watson | ................ | A61B 5/6802 |
| 2017/0304139 A1* | 10/2017 | Ross | ...................... | A61H 11/00 |
| 2020/0287569 A1* | 9/2020 | Ikegaya | ............. | H03M 13/036 |

\* cited by examiner

SYSTEMS AND METHOD FOR COMPRESSION CONTROL IN A WEARABLE COMPRESSION DEVICE

BACKGROUND

Compression garments are devices and articles of clothing that conform to, are attached to, or fit around a portion of a human or other living organism. In medical contexts, static compression garments provide support for people and can be applied to affect blood circulation. For example, compression garments can help prevent deep vein thrombosis and reduce swelling, especially while traveling. They can also be used to address lymphedema. In recreational contexts, compression garments can be worn during or after exercise to support specific areas of the body or to combat muscle soreness, pain, and fatigue.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings, According to embodiments of the disclosed subject matter, an active compression device includes a controller assembly, wherein the controller assembly includes processing circuitry configured to receive a selection of a predetermined compression profile. The selection of the predetermined compression profile may be made from a group of different predetermined compression profiles. Additionally, the processing circuitry is further configured to, in response to receiving the selection of the predetermined compression profile, actuate one or more shape memory wires integrated into the active compression device to apply a predetermined pattern of compressions corresponding to the selected predetermined compression profile. The predetermined pattern of compressions may have several compression components and variants. For example, the predetermined pattern of compressions applied to a wire may include a compression component that causes the wire to contract and expand over a certain period of time while, at the same time, another compression component is applied to the wire to cause perturbations along the wire as it expands and contracts in response to the first compression component.

According to embodiments of the disclosed subject matter, an active compression device includes a textile wrap configured to be secured around a waist of a user. Additionally, the active compression device includes a controller assembly disposed within the textile wrap, wherein the controller assembly includes one or more shape memory wires configured to apply compression to the user's back in response to actuation of the one or more shape memory wires. The controller assembly also includes processing circuitry configured to receive a selection of a predetermined compression profile, and in response to receiving the selection of the predetermined compression profile, activate a predetermined pattern of compressions corresponding to the selected predetermined compression profile. The predetermined pattern of compressions may have several compression components and variants. For example, the predetermined pattern of compressions applied to a wire may include a compression component that causes the wire to contract and expand over a certain period of time while, at the same time, another compression component is applied to the wire to cause perturbations along the wire as it expands and contracts in response to the first compression component. The other compression components may excite the wire to create "push and hold," "double bump," and/or "pulse" compression profiles.

According to embodiments of the disclosed subject matter, a method for implementing a predetermined compression profile includes receiving a selection of a predetermined compression profile for an active compression device. The selection of the predetermined compression profile may be made from a group of different predetermined compression profiles. In response to receiving the selection of the predetermined compression profile, the method can further include actuating one or more shape memory wires integrated into the active compression device to apply a predetermined pattern of compressions corresponding to the selected predetermined compression profile. The predetermined pattern of compressions may have several compression components and variants. For example, the predetermined pattern of compressions applied to a wire may include a compression component that causes the wire to contract and expand over a certain period of time while, at the same time, another compression component is applied to the wire to cause perturbations along the wire as it expands and contracts in response to the first compression component.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
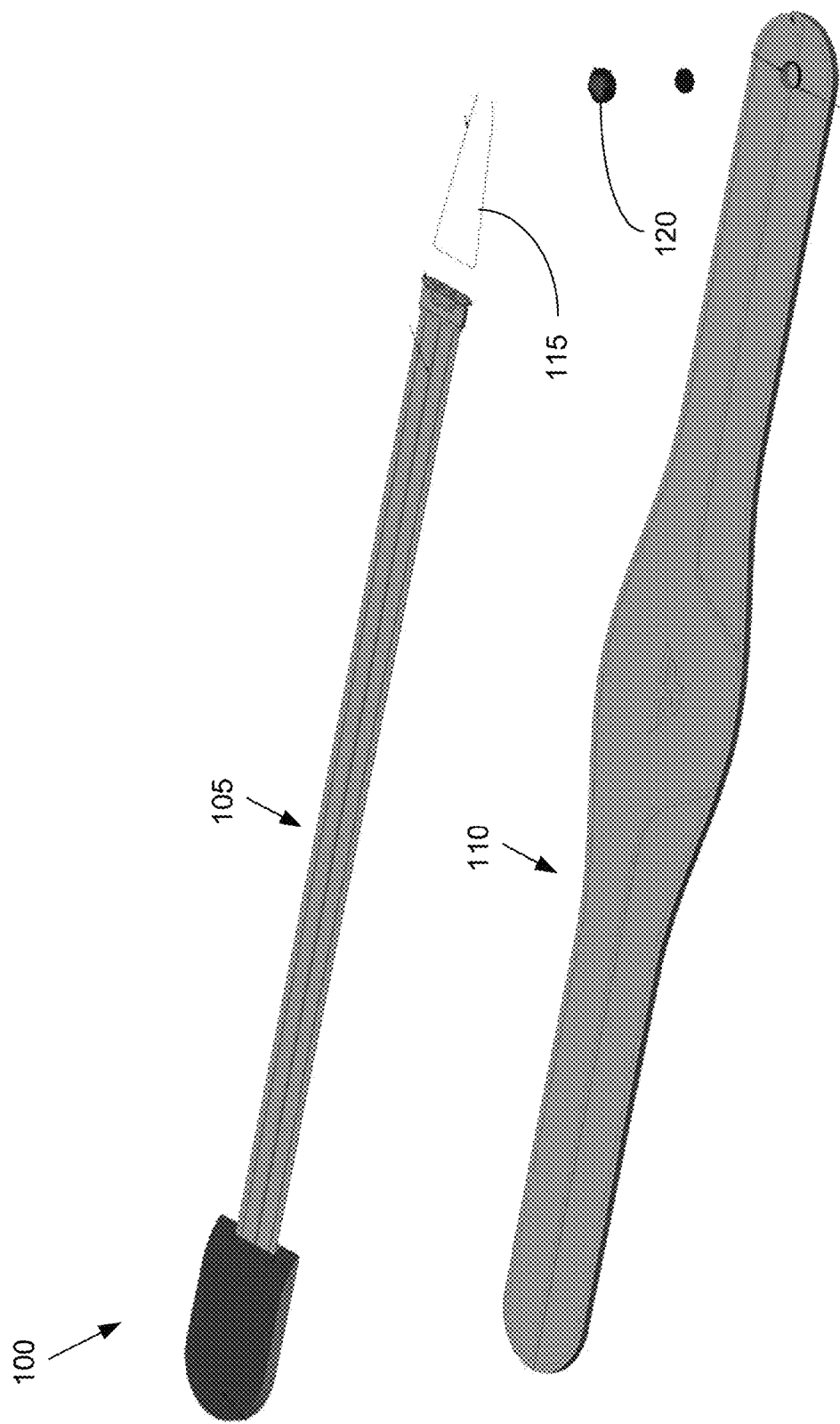
FIG. 1 depicts an exemplary overview of an active compression device according to one or more aspects of the disclosed subject matter.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

Reference throughout the specification to "one embodiment" or "an embodiment" means that a particular feature, structure, characteristic, operation, or function described in connection with an embodiment is included in at least one embodiment of the disclosed subject matter. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments. Further, it is intended that embodiments of the disclosed subject matter can and do cover modifications and variations of the described embodiments.

It must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the disclosed subject matter to any particular orientation or configuration. Furthermore, terms such as "first," "second," "third," etc., merely identify one of a number of portions, components, points of reference, operations and/or functions as described herein, and likewise do not necessarily limit embodiments of the disclosed subject matter to any particular configuration or orientation.

Compression garments are devices and articles of clothing that snugly conform to, are attached to, or fit around the skin of a human or other living organism. They have many applications. Compression garments that employ the subject matter disclosed in this detailed description can be used for many purposes, including to improve the effectiveness of the use of a compression garment in well-known applications.

For example, a compression garment can be used to create a soothing sensation. This soothing sensation may be applied to counteract pain, stress, or strain that exists in a particular area of a human body. A compression garment may also be used to brace an area of the body during when stress and strain is being exerted on that area. For example, workers that move heavy items are known to wear braces on their lower backs to counteract forces transferred to their lower backs while moving heavy items.

In medical contexts, compression garments can be used to address circulatory issues. They may also be worn to prevent or combat deep vein thrombosis and reduce swelling. These problems may arise more commonly in post-operative patients, the bedridden, those that suffer from ailments such as lymphedema or diabetes, and people, such as travelers, confined to tight spaces for long periods of time.

Compression garments can be used to enhance and decrease the flow of blood. Enhanced blood flow may be essential to some for quality of life, such as for those individuals suffering from peripheral vascular disease and restless leg syndrome, or women undergoing reconstructive breast surgery suffering from arm pain and fatigue due to poor blood flow.

Compression garments may also be used in recreational applications. Many athletes suffer from muscle soreness, pain, and fatigue after exercise due to toxins and other by-products that are released during periods of physical exertion. Research has shown that compression garments may provide ergogenic benefits for athletes by enhancing lactate removal, reducing muscle oscillation, and positively influencing psychological factors. Research has also shown that compression garments may serve both a performance enhancement and an injury reduction role during physical exertion by provoking high blood lactate concentrations.

Compression garments may also be used in high-speed and flight applications. For example, compression garments, known as G-suits, can be used to counteract g-forces. Compression garments, known as pressure suits, are used to provide pressure at high altitudes where the air pressure is too low for human survival.

Compression garments allow for varying degrees of compression. Higher degree static compression sleeves, such as sleeves that provide compression of 20-30 millimeters of mercury (mmHg) or higher, typically require a doctor's prescription.

Compression garments are typically static devices. In other words, they do not move on their own. Once a compression garment is fixed in place it provides an amount of force and support that correlates to the materials from which it is made, the position in which it was placed on the subject, and, if it can be varied upon application, the amount of tension the subject placed the garment under when fixing it in place. Compression garments that are not static devices, and thus that can compress and relax on their own, are bulky and slow because they are driven by gasses, such as air, or fluids, such as water.

It would be advantageous to have a compression garment that is not bulky and that can actively and dynamically compress and relax on its own, and, in doing so, reacts quickly to control inputs. Further, it would be advantageous for such a compression garment to be designed to have the capability of actively and dynamically compressing and relaxing different portions, segments, areas, or sections of the garment independently of other portions, segments, areas, or sections of the garment. Further, it would be advantageous for such a compression garment to be designed to produce and transfer known and controlled temperatures to the subject using the garment. Further, it would be advantageous for such a compression garment to be designed to vary known and controlled temperatures produced and transferred to the subject using the garment. Further, it would be advantageous for such a compression garment to have the capability of being programmed to operate in accordance with various active and dynamic compression and temperature generation profiles.

Referring now to the drawings, wherein like reference numerals designate identical or corresponding parts throughout the several views.

FIG. 1 depicts an exemplary overview of an active compression device 100 according to one or more aspects of the disclosed subject matter. The compression provided by the active compression device 100 can be applied to a portion of a person's body. Active compression garments utilizing the components and operational concepts disclosed and described in connection with the exemplary device of FIG. 1 and the remaining figures may be constructed to be applied to virtually any part or portion of the body of a human or other living organism. The compression can be applied to a user's foot, arm, calf, and other portions of the user's body in one or more implementations such as described in Pub. No.: US 2017/0252252, which is incorporated by reference herein in its entirety. The description of the active compression device 100 is directed toward a back brace implementation to be worn around a user's waist.

The active compression device 100 can include a controller assembly 105, a textile wrap 110, a Boa lace 115, and a Boa dial 120. As will be discussed in more detail, one or more methods according to various embodiments of the disclosed subject matter can be implemented using the active compression device 100 or portions thereof. In other words, the active compression device 100, or portions thereof, can perform the functions or operations described herein regarding the various methods or portions thereof (including those implemented using a non-transitory computer-readable medium storing a program that, when executed, configures or causes a computer to perform or cause performance of the described method(s) or portions thereof).

Generally speaking, the active compression device 100 can utilize shape changing materials to apply compression. It may also contain material that, separate from or the same as the shape changing material, conducts and releases heat. For example, the shape changing materials can include a shape memory metal alloy implemented as a shape memory wire (e.g., Nitinol wire).

More specifically, the active compression device 100 can include a plurality of shape changing elements that are operable to change shape in response to an external stimulus. This change of shape effectively reduces the circumference of the active compression device 100 encircling the user, thereby applying pressure or a compressive force to the user. In one embodiment, the shape changing element is an element configured to change length, and more particularly to reduce its length in response to the stimulus. The plurality of shape changing elements can be one or more wires formed of a "shape memory" material or alloy that shrinks when a current is applied to the wire, and that returns to its original "memory" configuration when the current is removed or changed.

The active compression device 100 can include a wire array 105 that spans a length of the active compression device 100. The wire array 105 can be configured to reduce the diameter of the active compression device 100 in response to the wire array being activated when being worn by a user. In one or more embodiments, the wire array 105 can include wires formed of a "memory" material that changes length upon application of an electrical signal and then returns to its original length when the signal is terminated. Thus, each of or groups of the wires of the array can be selectively stimulated, or activated, and deactivated to create varying amounts of compressive forces on a user wearing the controller assembly 100. The memory material can be a memory metal such as Nitinol.

Electroactive polymers (EAP) can also be used in place of the Nitinol wires. EAPs are polymers that can exhibit a change in size and/or shape when stimulated by an electric field. As a result, they can be controlled in predetermined compression patterns like the Nitinol wires.

The active compression device 100 can include processing circuitry configured to receive a selection for predetermined compression profiles and heat settings. The predetermined compression profiles can include, for example, a compression force target of around 6 pounds of force, with a tolerance of +/−0.50 pounds. The force target can include a range/tolerance based on variations from components and materials (e.g., Nitinol transition temperature, electrical components, controller assembly tolerances, etc.). Additionally, the active compression device 100 may include various other functionality, including the ability to energize a Nitinol engine, monitor battery usage and charge, keep time of an active session, store engine usage, and log any errors.

The active compression device 100 can also include a power source (e.g., a lithium ion battery) to power the Nitinol engine and other electronic components.

The textile wrap 110 can provide thermal insulation to a wearer of the active compression device 100. Additionally, the textile wrap 110 can be bio-compatible, comfortable, and have a low coefficient of friction so as not to impede the performance of the Nitinol engine. The textile wrap 110 can protect the Nitinol engine and electronics from the environment. Further, the bio-compatibility between the textile wrap 110 and a user should be configured so the performance of the Nitinol engine (i.e., expected compression profile and heat) is not impeded. The textile wrap 110 may be formed of a generally inelastic or only moderately "stretchable" material that is suited for contact with the skin of the user. The material of the fabric body may be a breathable material to reduce perspiration or may be a generally impermeable material to enhance heating of the body part under compression treatment. In one embodiment, the textile warp 110 can be a compressible body having a thickness to accommodate the shape-changing elements described herein. The textile wrap 110 may include one or more pockets or sleeves to receive and retain the controller assembly 105. It is further contemplated that the textile wrap 110 may be configured so that the controller assembly 105, or portions thereof, is sewn into the textile wrap to secure the controller assembly 105 within the textile wrap 110. In one or more embodiments, the textile wrap 110 is an elastic 3-layer material made of polyurethane foam with smooth knit material bonded on both sides.

In one or more embodiments, a transition temperature of the Nitinol wires varies depending on the amounts of Nickel and Titanium in the wires. Typical wires compositions can have transition temperatures that vary from 70 degrees Celsius to 80 degrees Celsius. Although 70 to 80 degrees Celsius may be uncomfortable or dangerous for direct contact on a user's skin, the active compression device 100 can be configured to control the temperature of the Nitinol wires to both improve performance of the Nitinol wires and reduce the temperature to an acceptable level by the time the heat reaches the skin of the user. For example, to use the active compression device 100 in a Class 1 & 2 medical environment, the temperature needs to be less than 41 degrees Celsius when contacting the user's skin. More specifically, the temperature is measured between the outer layer of the textile wrap 110 and the user's body. To achieve the improved wire performance, Teflon tape included as part of the textile wrap 110 can control the transition temperature of the Nitinol wire by both insulating the Nitinol wires and acting as a heat sink. By drawing the heat away from the Nitinol wires, the Teflon tape can improve the performance of the Nitinol wires by controlling the response time in how fast the Nitinol wires heat up. By insulating the Nitinol wires, the Teflon tape can also control how fast the Nitinol wires cool. A visual representation of this can be seen in the graphs in FIGS. 4A-C and 5A-C where the slope while energizing the wire (positive slope) corresponds to how fast the wire heats up. After the wire is no longer energized, the negative slope shows the controlled decrease in temperature. Additionally, the temperature can be controlled such that the user can experience a high or low heat setting when wearing the active compression device 100, and the Teflon tape is the first step in transferring the heat from the Nitinol wires to the user. Additionally, because the temperature measurement for the Class 1 & 2 medical environment occurs between an outer layer of the textile wrap 110 and the user's body, the Teflon tape and the textile wrap 110 can sufficiently control the temperature to an acceptable level when measured between the outer layer of the textile wrap 110 and the user's body.

As a result, the active compression device 100 can be implemented within a Class 1 & 2 medical environment. More specifically, within the Class 1 & 2 medical environment, the active compression device 100 should exhibit certain performance characteristics including that the heat exerted onto a user can be maintained to be less than 41 degrees Celsius.

Additionally, the Teflon tape can structurally secure the Nitinol wires in a predetermined location in the controller assembly. For example, each Nitinol wire can be held at least substantially in the same plane to provide even compression when the active compression device 100 is being worn by a user, as well as positioning each Nitinol wire a predetermined distance from another Nitinol wire or a ground wire.

Alternatively, or additionally, other substrates with similar heat transfer and elastic properties as Teflon tape can be used.

Generally, the Nitinol wires can be pretensioned mechanically. More specifically, the Boa lace 115 can be connected to the Boa dial 120 and used to pretension an engine (e.g., Nitinol engine 240 in FIG. 2). For example, the Boa lace 115 can be attached to the Nitinol wires in the controller assembly 105, which can be pretensioned in response to manipulation of the Boa lace 115 via the Boa dial 120. As a result of the manipulation of the Nitinol wires 245 via the Boa lace 115 and the Boa dial 120, the Nitinol engine 240 can be pretensioned. The Nitinol wires in the controller assembly may be preferably pretensioned at around 1.0 pound of force.

In one or more embodiments, the active compression device 100 can be a wearable compression device. More specifically, the active compression device 100 can be a back compression device. For example, the active compression device 100 can be secured around a waist of the user and activated to deliver compression and heat to the user as further described herein.

Figure 2:
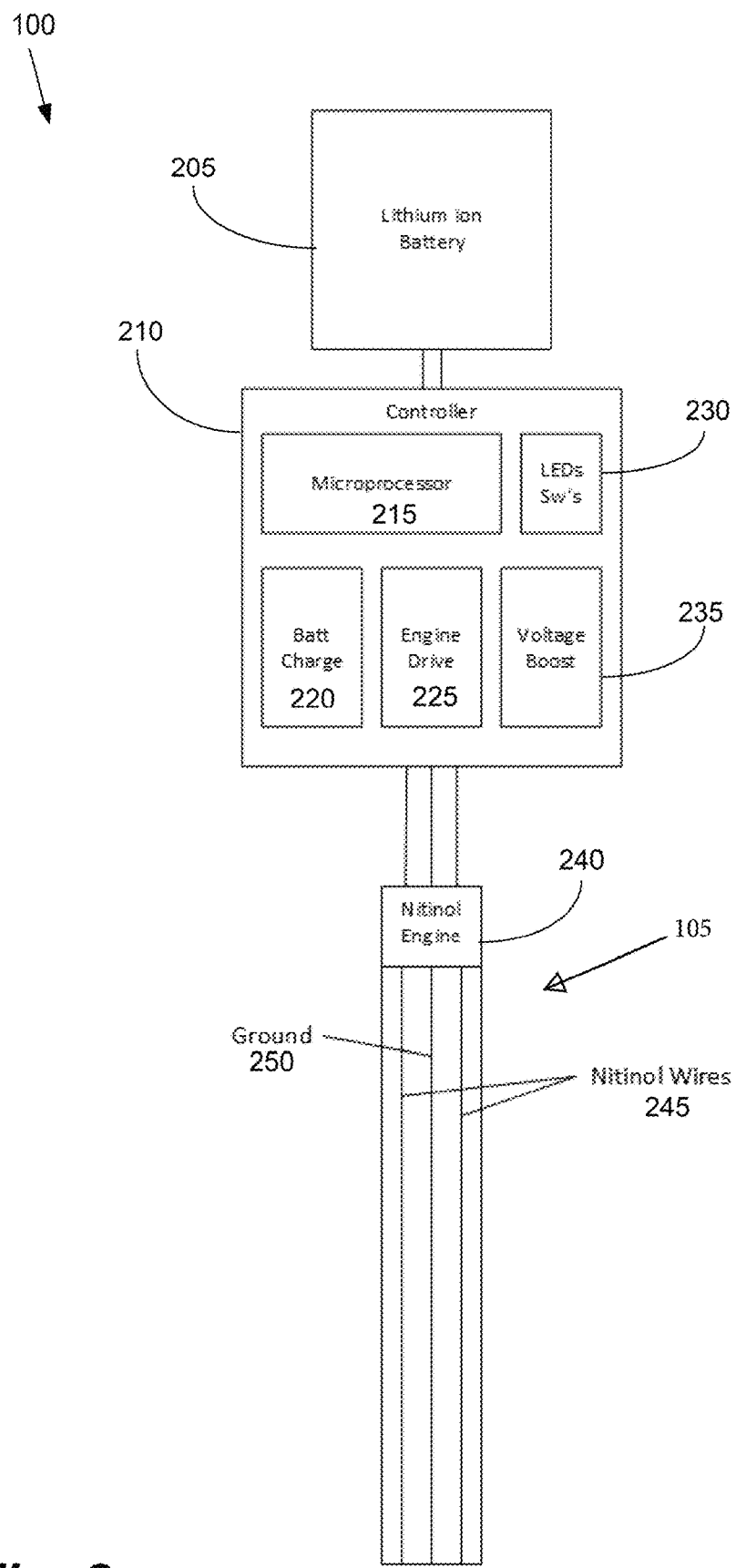
FIG. 2 depicts an exemplary hardware block diagram of a controller assembly according to one or more aspects of the disclosed subject matter.

FIG. 2 depicts an exemplary hardware block diagram of the controller assembly 105. The controller assembly 105 can include a lithium ion battery 205, a controller 210, a Nitinol engine 240, Nitinol wires 245, and a ground 250. Additionally, the controller 210 can include a microprocessor 215, a battery charge 220, an engine drive 225, LEDs 230, and a voltage boost 235.

Generally, the Nitinol wires 245 are an alloy of nickel and titanium that when in a shape-memory state, can undergo a molecular reconfiguration in response to a predetermined temperature change. For example, the Nitinol wires 245 can contract in response to being heated above a predetermined transformation temperature corresponding to the Nitinol wires 245, and return to its original state when cooled. The transformation temperature is a predetermined temperature based on the characteristics of the Nitinol wire (e.g., shape, size, composition, etc.). Although Nitinol exhibits superior characteristics over other metals, stress in the form of over-heating or high forces can have a negative impact on the life of the wire. Under expected operating conditions, Nitinol can be subjected to millions of cycles. However, under stressful conditions, Nitinol may fail with only 100 to 1000 cycles.

More specifically, each of the Nitinol wires 245 can correspond to a single channel that can be individually actuated during a compression treatment. Each of the Nitinol wires 245 can be part of the Nitinol engine 240, and the Nitinol engine 240 is connected to the controller 210. The engine drive 225 can energize and de-energize the Nitinol wires 245 within the Nitinol engine 240 based on firmware programmed into the microprocessor 215. The energizing and de-energizing causes the Nitinol wires 245 to contract (e.g., shorten) and relax (e.g., elongate), thus providing the active compressions when the active compression device 100 is applied to a user's body. Further, the microprocessor 215 can control a sequence and magnitude of a current applied to each of the Nitinol wires 245 simultaneously or independently. In one embodiment, the microprocessor 215 may be preprogrammed with one or more particular compression sequences for a particular user and corresponding active compression device 100. The active compression device 100 may be distinguished based on a length of the Nitinol wire which may affect the one or more particular compression sequences, as further described below. The compression sequence may include an infinite or continuous rolling in which the active compression device 100 is successively compressed around a user's body similar to a peristaltic movement, a step-wise sequence in which the active compression device 100 is compressed and held for a period, or even a random sequence. Other compression protocols may be preprogrammed into the microprocessor 215 that can be selected by the user as desired.

In one or more embodiments, the controller 210 can be a Parallax microcontroller. More specifically, the controller 210 can be the Parallax microcontroller Part No. BS2-IC.

When at least one of the Nitinol wires 245 is activated, the microprocessor 215 can direct current to the specific wire or wires, thereby causing one or more of the Nitinol wires 245 to contract or shrink, thereby reducing the effective diameter of the Nitinol wires or wires when wrapped around a user. This reduction in diameter translates to an application of pressure by way of the active compression device 100 which is in contact with the user, and can be designed to be secured around the user's waist. When the current is removed or changed, the "memory" feature of the Nitinol wires 245 allows them to return to a deactivated or neutral condition, thereby removing pressure from the associated textile wrap 110. In addition, the user's body can act as a spring to assist in returning the memory wire(s) to the neutral phase.

One end of each of the Nitinol wires 245 can be connected to the Nitinol engine 240. Generally, the Nitinol engine 240 can provide active compressions and therapeutic heat. More specifically, the Nitinol engine 240 can be configured to provide electrical current to each Nitinol wire 245 via the instruction of the microprocessor 215. Electrical current can be applied to the Nitinol wires 245 at contact mounts to heat the wires ohmically beyond a predetermined transition temperature and to cause the Nitinol wires 245 to change length or contract, thereby applying compression via the active compression device 100. As further described herein, the electric current can be applied in specific patterns to create predetermined compression profiles and heat settings. Additionally, due to the heating of the Nitinol wires, the Nitinol wires 245 can be encapsulated in Teflon tape that provides electrical, moisture, and thermal insulation. The insulation provided via the Teflon tape can be a first mechanism to control heat created from the electrical current being applied to the Nitinol wires 245. The heat can be controlled so the user gets the therapeutic benefits provided by the heat while still maintaining a temperature that meets various medical standards.

The Nitinol engine 240, and therefore the Nitinol wires 245, can be pretensioned to enable the wires to return to their original position quickly once cooled. The pretensioning can be achieved via the Boa lace 115 and Boa dial 120. The Boa lace 115 can be connected to the Boa dial 120 via a predetermined laced pattern so that the Boa dial 120 can manipulate the Boa lace 115. Manipulation of the Boa lace 115 via the Boa dial 120 can be used to pretension the Nitinol engine 240, thereby pretensioning the Nitinol wires 245, and the Nitinol wires 245 are preferably pretensioned to 1 pound of force. In one or more embodiments, the pretensioning can be achieved by configuring the textile wrap 110 to be an elastic fabric case where stretching the fabric when securing the active compression device 100 (e.g., putting the active compression device 100 on like a belt) can sufficiently pretension the Nitinol wires.

The controller 210 can include a power supply. The power supply can be the lithium ion battery 205, which is preferably a rechargeable battery that can be recharged via battery charge 220.

The controller 210 can additionally include a voltage boost 235. The voltage boost 235 can be utilized to accommodate the change in operating voltage of the battery from fully charged to the battery requiring a charge to the battery having low voltage. As a result, the voltage boost 235 can be incorporated and implemented based on equation 1 and equation 2 below.

The controller 210 can additionally include LEDs 230. The LEDs 230 may be configured to be indicator lights for various power indication, compression settings, heat settings, and the like. For example, one or more LEDs may light up in one or more combinations and/or sequences to indicate the various functionality of the active compression device 100.

Figure 3:
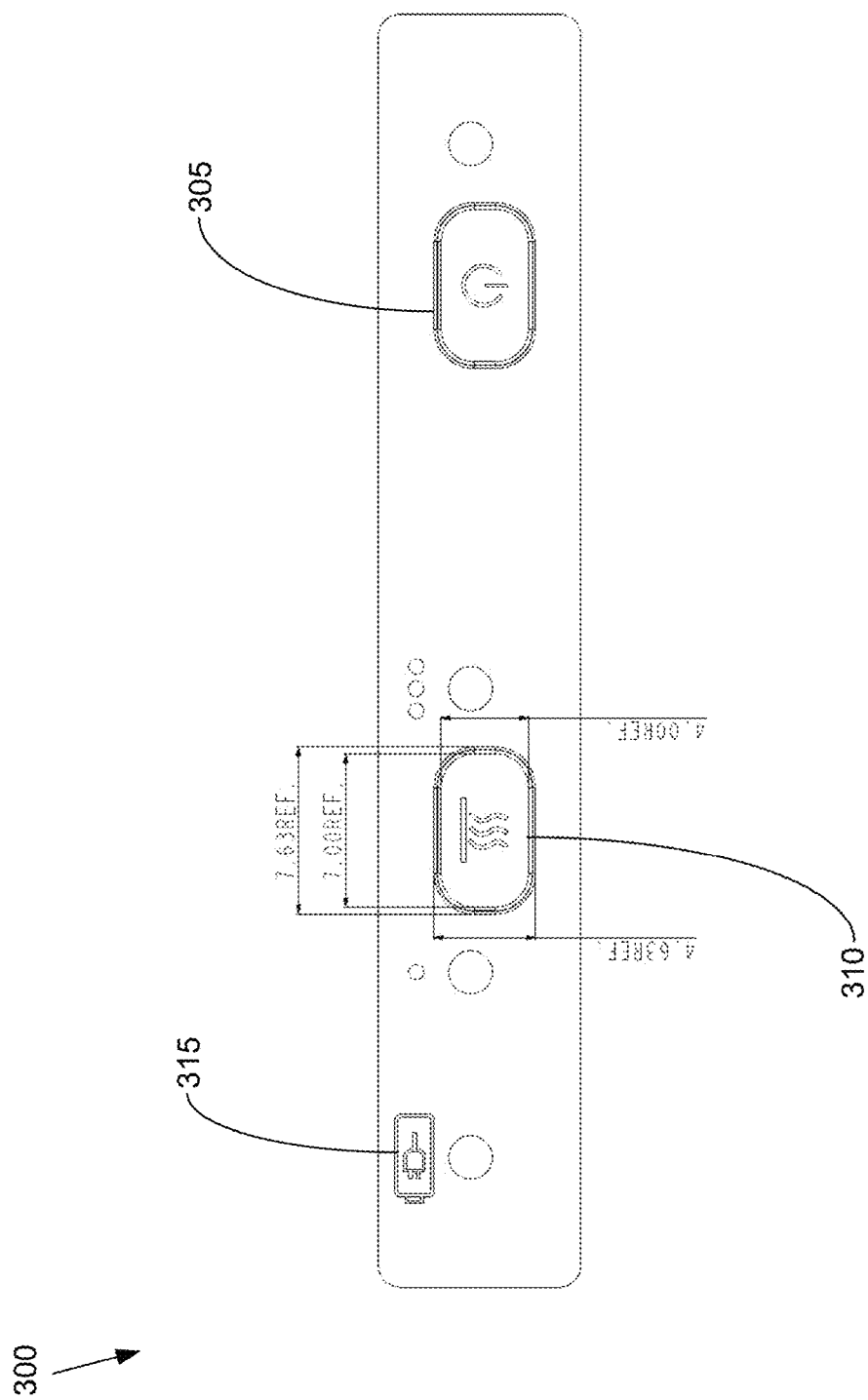
FIG. 3 depicts an exemplary interface for interacting with an active compression device according to one or more aspects of the disclosed subject matter.

FIG. 3 depicts an exemplary interface 300 for interacting with the active compression device 100 according to one or more aspects of the disclosed subject matter. The active compression device 100 can have basic user controls accessibly embedded in the active compression device 100. The basic user controls can be included in the interface 300. The user can interact with the basic user controls via the interface 300 to instruct the microprocessor 215 to implement a predetermined sequence and pattern of compression based on a selected compression profile and heat setting. The interface 300 can be disposed in a predetermined location on the active compression device 100, preferably accessible to the user. For example, the interface 300 may be accessible through the textile wrap 110. The interface 300 can be electrically connected to the controller 210 such that the controller 210 can receive input from a user via the interface 300 and transmit corresponding instructions to the relevant components of the controller assembly 105. To provide such interaction, the interface 300 can include a power button 305, a function button 310, and a charge indicator 315.

The power button 305 can turn the active compression device 100 on and off. The charge indicator 315 can indicate a remaining charge in the power source (e.g., lithium ion battery 205) of the active compression device 100. The function button 310 can be configured to select from a plurality of compression profiles and heat settings. In other words, the function button 310 can be configured to instruct the microprocessor 215 to implement a predetermined compression profile and/or heat setting. The function button 310 can be pressed once to select a first predetermined option, long pressed (e.g., longer than 3 seconds), and/or the function button 310 can be pressed a plurality of times to cycle through additional compression profile and/or heat setting options.

Figure 4A:
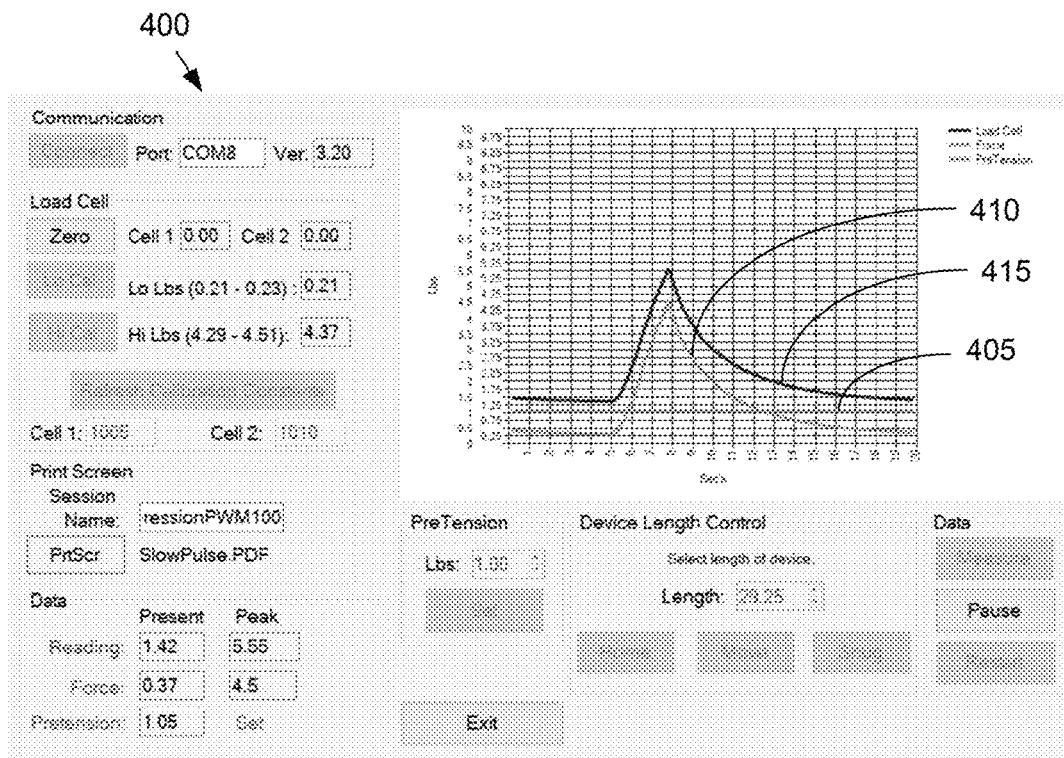
FIG. 4A depicts an exemplary graphical representation of a full compression profile according to one or more aspects of the disclosed subject matter.

FIG. 4A depicts an exemplary graphical representation of a full compression profile 400 according to one or more aspects of the disclosed subject matter. Generally, a full compression profile can represent the force (shown in pounds on the X-axis of the graphical readout) applied by the active compression device 100 over time (shown in seconds on the Y-axis of the graphical readout). The full compression profile 400 indicates one compression cycle of the active compression device 100, where the force created by the active compression device 100 can increase until reaching a peak force and then decrease based on a predetermined pattern of energizing and cooling the Nitinol wires 245 in the active compression device 100.

Figure 4B:
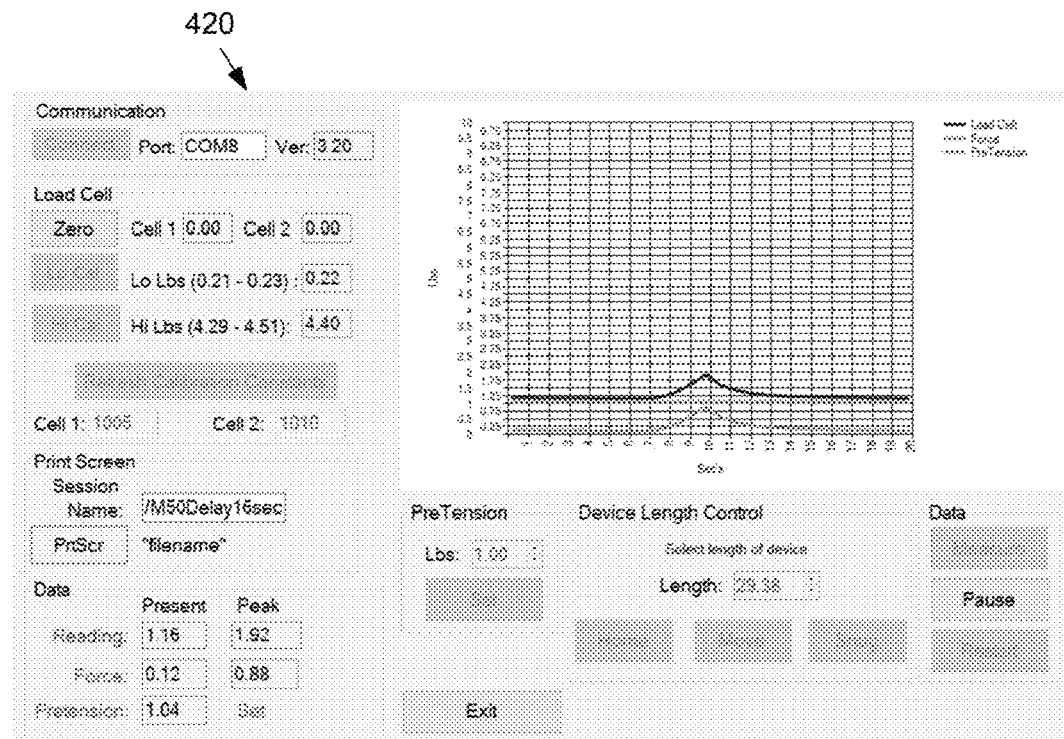
FIG. 4B depicts an exemplary graphical representation of a full compression profile according to one or more aspects of the disclosed subject matter.
Figure 4C:
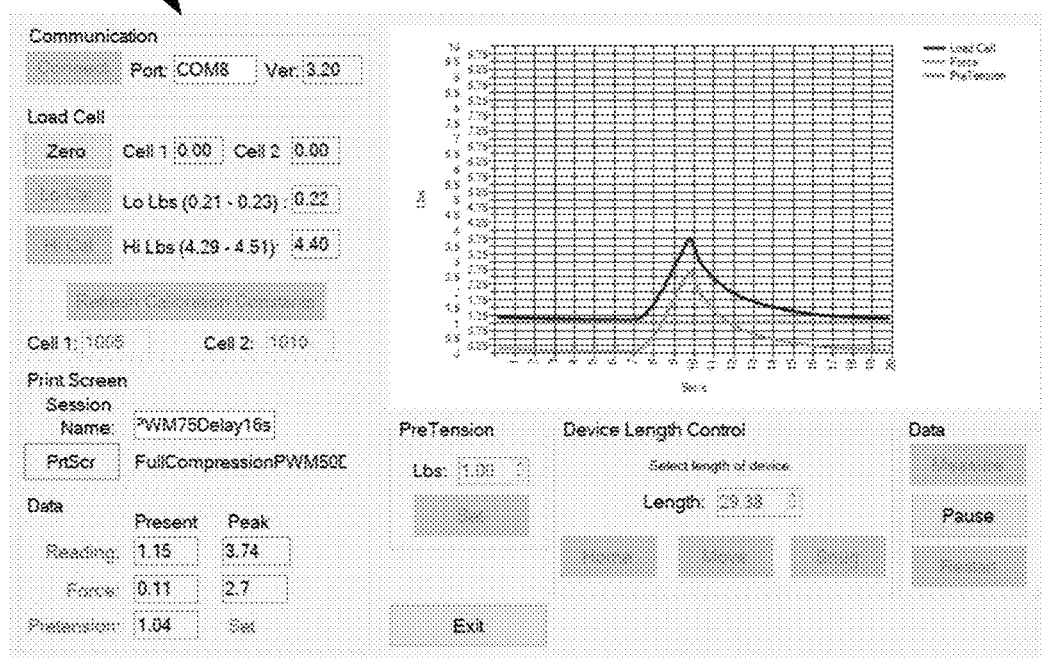
FIG. 4C depicts an exemplary graphical representation of a full compression profile according to one or more aspects of the disclosed subject matter.

In other words, the full compression profiles in FIGS. 4A-4C can be utilized to display a visual representation of a compression profile based on energy input parameters. The energy input parameters can include a power provided to the Nitinol engine 240 via pulse width modulation when activating the Nitinol wires 245. For example, the power may be modulated based on the size (i.e., length of the Nitinol wires 245) of the active compression device 100. Analysis of the results of the energy input parameters can be used to determine optimal energy input parameters for each size of the active compression device 100. The full compression profile 400, as well as the compression profiles described in FIGS. 4B, 4C, and 5A-5C, is measured using an active compression device test stand (e.g., test stand 805) as further described in FIGS. 8, 9, and 10.

The full compression profile 400 can include a peak force reading. The peak force can correspond to the maximum force in a compression cycle. Additionally, line 405 is the pretension value, wherein the pretension value can correspond to the force applied via the Boa lace 115 because the Nitinol wires 245 can preferably be pretensioned at about 1 pound for optimal operation. Line 415 represents a real-time force reading corresponding to a compression cycle. Line 410 represents the pretension value 405 subtracted from the real-time force 415.

The graphed pressure data not only depicts the pressure curve, hut also reveals the cooling of the Nitinol wire (e.g., Nitinol wires 245). If the real-time force (e.g., line 415 of compression profile 420) does not intersect the pretension value, then the Nitinol wire is not fully cooling. In other words, the real-time force not intersecting the pretension value indicates that the Nitinol wire is not returning to its starting force, wherein the starting force is the pretension force set when the Nitinol wire is cooled and not energized. Although some predetermined compression profiles may specifically energize the wire before allowing it to fully cool to create a high heat setting, it is important that the Nitinol wires 245 are able to fully cool to prevent unnecessary wear and tear that may limit the lifetime of the Nitinol wires.

FIG. 4B depicts an exemplary graphical representation of a full compression profile 420 according to one or more aspects of the disclosed subject matter. The full compression profile 420 in FIG. 4B is the graphical representation of the same active compression device in FIG. 4A but energized at 50% power. The full compression profile 420 shows a decrease in force as well as peak pressure. Similarly, FIG. 4C depicts a full compression profile 440 of the same active compression device as FIG. 4B but energized at 75% power. The full compression profiles 400, 420, and 440 can be utilized to determine optimal energy input parameters. Determining optimal energy input parameters can significantly increase the lifetime of the Nitinol wires (e.g., millions of cycles) by avoiding stressful conditions that may cause a Nitinol wire to fail with only 100 to 1000 cycles. In other words, graphical representations of the 50% (FIG. 4B), 75% (FIG. 4C), and 100% (FIG. 4A) power settings are examples of the effects of the forces generated via the active compression device 100. Based on FIGS. 4A-4C, the effect of a predetermined amount of power to activate the active compression device 100 can be seen clearly, and the information can be utilized in determining optimal energy input parameters. Additionally, the graphical representations of the forces generated via the active compression device 100 can provide confirmation of the correct timing and sequences of energizing and cooling the Nitinol wires for any predetermined compression profile, as shown in FIGS. 5A-5C.

Figure 5A:
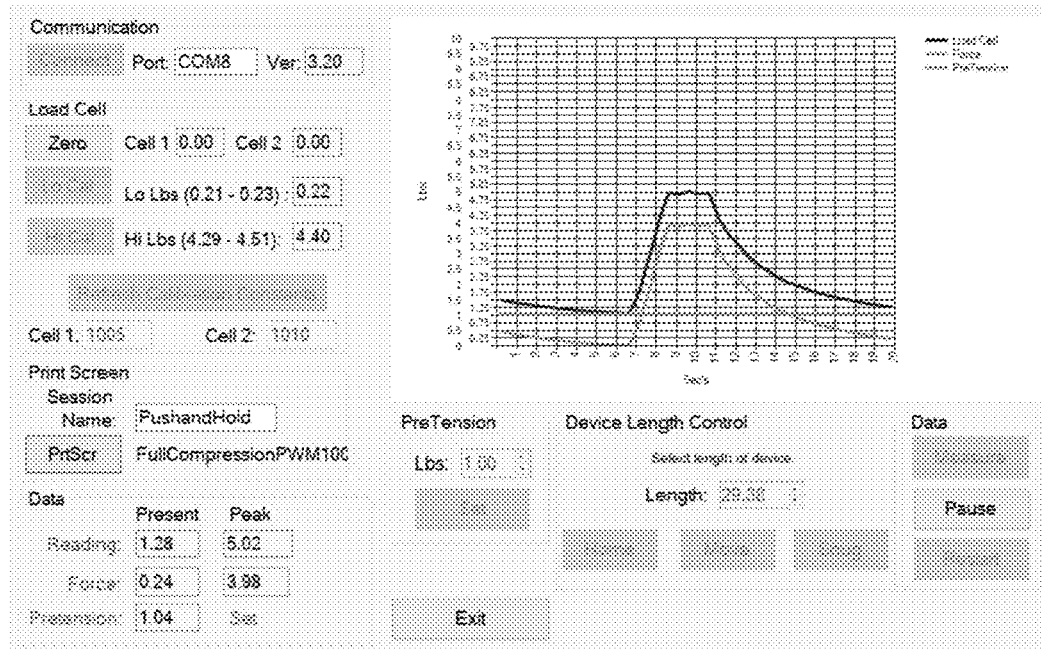
FIG. 5A depicts an exemplary graphical representation of a first predetermined compression profile according to one or more aspects of the disclosed subject matter.
Figure 5B:
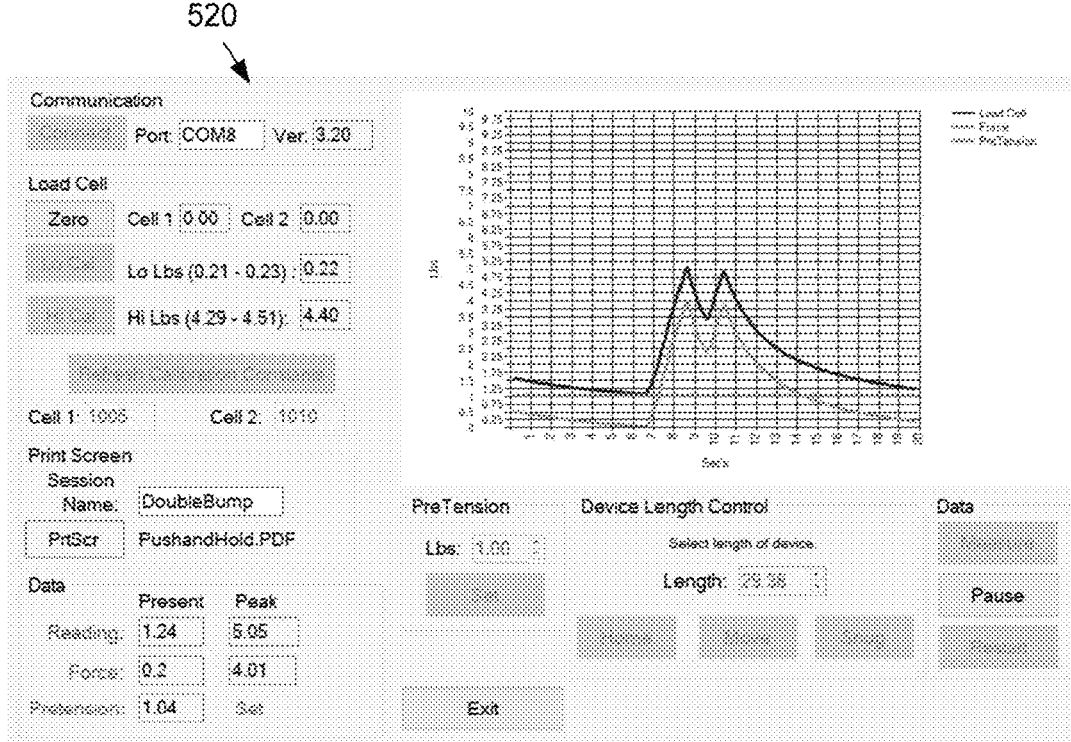
FIG. 5B depicts an exemplary graphical representation of a second predetermined compression profile according to one or more aspects of the disclosed subject matter.
Figure 5C:
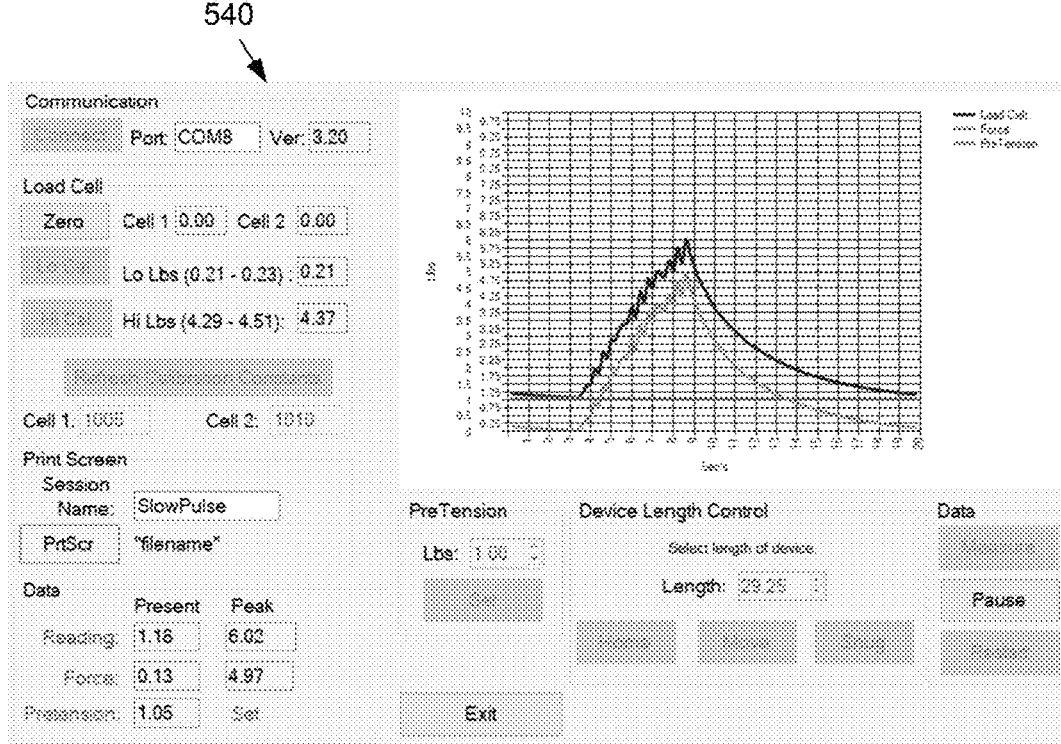
FIG. 5C depicts an exemplary graphical representation of a third predetermined compression profile according to one or more aspects of the disclosed subject matter.

FIGS. 5A-5C depict exemplary graphical representations of predetermined compression profiles according to one or more aspects of the disclosed subject matter. FIG. 5A depicts a "push and hold" compression profile 500. The "push and hold" compression profile 500, as well as the "double bump" compression profile 520 (FIG. 5B) and the "slow pulse" compression profile 540 (FIG. 5C), can correspond to a predetermined pattern of compression applied by the active compression device 100. The predetermined pattern can be achieved by heating the Nitinol wires 245 for a first predetermined amount of time, and then allowing the Nitinol wires 245 to cool for a second predetermined amount of time. In addition to the main pattern of an overall increase in force and a subsequent decrease in force, the Nitinol wires 245 can be further manipulated during the overall increase and/or decrease in force. For example, with reference to FIG. 5C, the "slow pulse" compression profile 540 may include manipulating the Nitinol wires 245 with a predetermined pattern while the overall force is still increasing. An example of this using specific values for a predetermined compression profile is described with reference to Table 3.

FIG. 5B depicts an exemplary graphical representation of a "double bump" compression profile 520, and FIG. 5C depicts an exemplary graphical representation of a "slow pulse" compression profile 540. The compression profile 520 and the compression profile 540 are multi-power profiles, meaning a power value can be applied to one or more of the Nitinol wires 245 for a specific time, and then the power can be altered for a second specific amount of time. By changing the power and the time period, a specific profile can be achieved. The graphical representations from FIGS. 4A-4C and FIGS. 5A-5C can be utilized for compression profile development. In other words, without a means of measuring and visualizing the force curve, these specific profiles (including the compression profiles from Table 2 and Table 3) may not be developed as accurately, thereby adding unnecessary stress to the Nitinol wires 245 and reducing the lifetime of the wires as a result.

Commercial lithium ion batteries are constrained by the amount of current they can safely deliver, the number of charges, and the recharge voltage. The amount of current a lithium ion battery can deliver is defined by the "C" rating. The "C" rating of a battery (or cell) is used to indicate the continuous current draw (amps) the cell will support. By multiplying the "C" rating and the cell capacity in milliampere hours (mAh), the continuous current in milliamperes (mA) of a cell can be calculated. Considering an active compression device with a 3 cell, 11.1 volt, 800 mAh battery with a 7C rating, the continuous current that may be drawn out of the battery is 800 mAh×7=5600 mA, or 5.6 Amps. To accommodate the change in operating voltage of the battery from fully charged to the battery requiring a charge (fully charged=12.6 volts) to low battery voltage (80%*11.1 volts=8.88 volts), a boost circuit can be incorporated with a 20-volt output. The 20-volt boost voltage can be derived by matching pressure and voltage across all Nitinol wire lengths and various boost voltages.

Using Ohms law, the Nitinol wire current values can be calculated.

For example, Nitinol wire current requirement can be based on $$\text{amps}=\text{voltage}/\text{resistance}. \quad (\text{Eq. 1})$$

Using Eq. 1:

$$20 \text{ volts}/8.1 \text{ ohms}=2.47 \text{ amps}.$$

Further, the battery current requirement can be calculated with consideration of the boost circuit as follows:

$$\text{battery current}=((\text{Nitinol current}*\text{boost voltage})/85\% \text{ efficiency})/\text{battery voltage}. \quad (\text{Eq. 2})$$

Using Eq. 2:

$$\text{battery current}=((2.47*20)/0.85)/11.1=5.03 \text{ amps}.$$

Resistance of the Nitinol wire (e.g., Nitinol wires 245) is based on various characteristics including a length and a diameter of the Nitinol wire. Assuming a predetermined diameter for each length of Nitinol wire, the Nitinol current and battery current can be calculated using Eq. 1 and Eq. 2, and the results are display in Table 1.

TABLE 1

| Device Size | Length (inches) | Resistance (ohms) | Nitinol current (amps) | Battery current (amps) |
|---|---|---|---|---|
| Extra small | 24 | 8.1 | 2.47 | 5.03 |
| Small | 24 | 8.1 | 2.47 | 5.03 |
| Medium | 28 | 9.7 | 2.06 | 4.37 |
| Large | 32 | 10.8 | 1.85 | 3.92 |
| Extra Large | 36 | 12.2 | 1.64 | 3.48 |

In one or more embodiments, a boost circuit using 20 volts can be used for the active compression device 100. To accommodate a standard boost voltage and maintain a maximum pressure (e.g., 6.0 lb) on all Nitinol engines (e.g., Nitinol engine 240), the Nitinol engines can be controlled using Pulse Width Modulation (PWM). Each active compression device 100 can be tested and appropriate PWM values can be established that correlate to the 6.0 lb maximum pressure for each compression profile. The active compression device 100 can have a plurality of compression profiles, each with a high/low heat setting. For example, the active compression device 100 can have three compression profiles, which corresponds to six PWM values for each active compression device 100. Additionally, an on-time and off-time can be determined for each compression profile and each size of the active compression device 100, wherein the size of the compression device is based on the length of the Nitinol wires for that device. The PWM, on-time, and off-time for both a high and low heat setting for each compression profile for each size of the active compression device 100 is in Table 2.

In one or more embodiments, the active compression device 100 may implement compressions with approximately six pounds of peak force. Each force target can have a range/tolerance based on variations from components and materials (e.g., Nitinol transition temperature, electrical components, controller assembly tolerances, etc.). As a result, a typical tolerance may be 6.0+−0.50 pounds. When testing the active compression device 100, one or more of the energy input parameters, Table 2 values, and Table 3 values may be determined based on attempting to reach compressions within a predetermined tolerance of six pounds of peak force.

Figure 6:
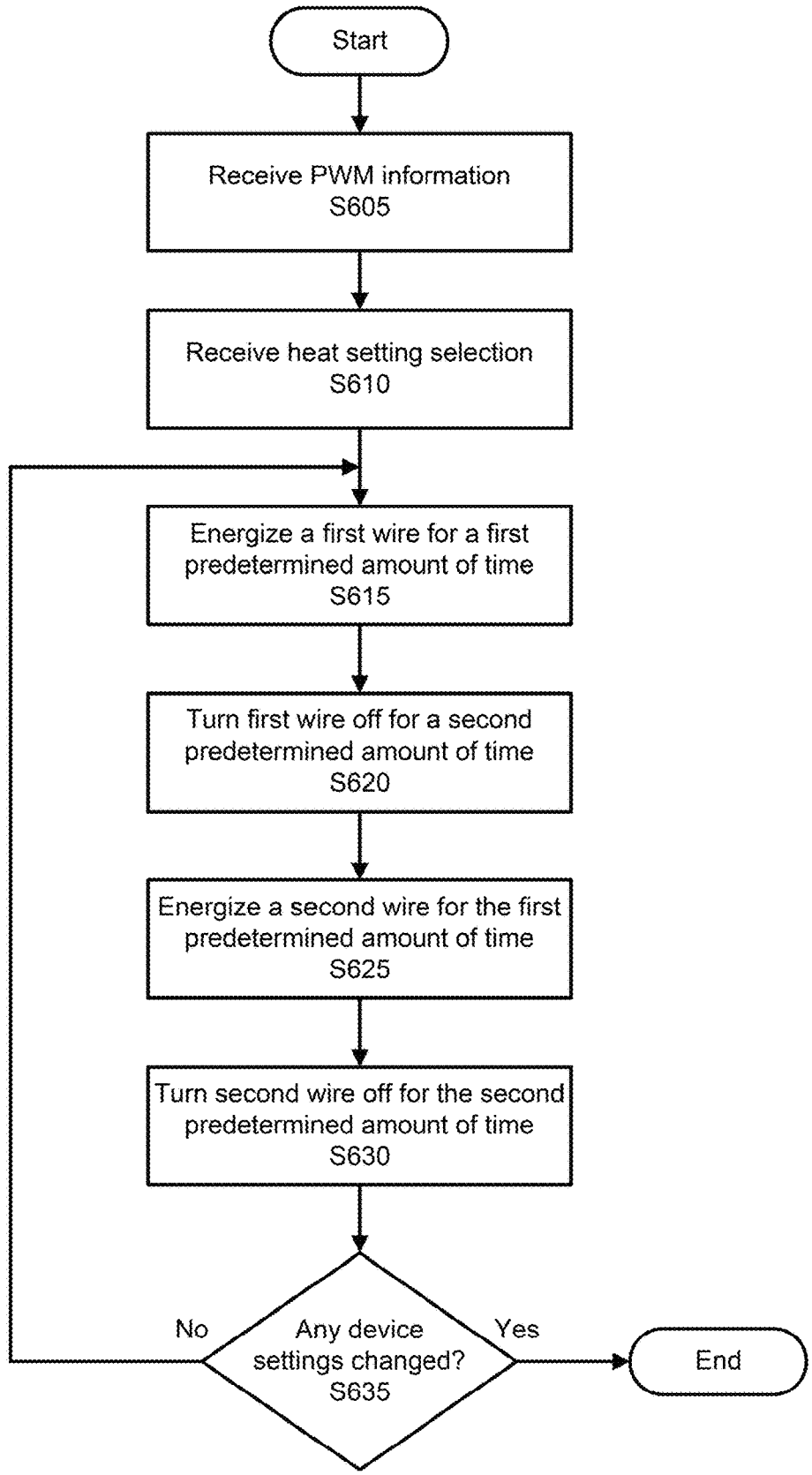
FIG. 6 is an algorithmic flow chart of a method for implementing a predetermined compression profile according to one or more aspects of the disclosed subject matter.

FIG. 6 is an algorithmic flow chart of a method for implementing a predetermined compression profile according to one or more aspects of the disclosed subject matter.

TABLE 2

| | Profile | | | | | | | | | | | | | | | | | |
|---|---|---|---|---|---|---|---|---|---|---|---|---|---|---|---|---|---|---|
| | Full Contraction | | | | | | Slow Pulse | | | | | | Fast Pulse | | | | | |
| | | | | | | | Heat Mode | | | | | | | | | | | |
| | Low | | | High | | | Low | | | High | | | Low | | | High | | |
| Parameters | PWM | On | Off | PWM | On | Off | PWM | On | Off | PWM | On | Off | PWM | On | Off | PWM | On | Off |
| Small | 95 | 2.5 | 14 | 95 | 2.5 | 11 | 140 | 3.0 | 16 | 140 | 3.0 | 13 | 255 | 3.0 | 16 | 225 | 3.0 | 13 |
| Med | 130 | 2.5 | 14 | 130 | 2.5 | 11 | 195 | 3.0 | 16 | 195 | 3.0 | 13 | 255 | 3.0 | 16 | 255 | 3.0 | 13 |
| Large | 145 | 2.5 | 14 | 145 | 2.5 | 11 | 220 | 3.0 | 16 | 220 | 3.0 | 13 | 255 | 3.0 | 16 | 255 | 3.0 | 13 |
| XLarge | 185 | 2.5 | 14 | 185 | 2.5 | 11 | 240 | 3.0 | 16 | 240 | 3.0 | 13 | 255 | 3.0 | 16 | 255 | 3.0 | 13 |

To standardize the voltage used for each of the different lengths of Nitinol wires (and therefore the corresponding sized active compression device 100), a single voltage can be used and the PWM can be changed to accommodate. Because it is advantageous to avoid different circuit board configurations for different sized active compression devices 100, 20 volts can be used across the entire platform for different lengths. In order to use 20 volts for each different sized active compression device, the PWM can be changed. The PWM can correspond to the power provided to the Nitinol wires. More specifically, a PWM value of 0 corresponds to the power being completely off, and a PWM value of 255 corresponds to the power being completely on. For a smaller active compression device, the PWM values can be significantly less than for the X-large sized active compression device 100 depending on the compression profile. In other words, the PWM value adjusts the power to the Nitinol engine 240, and then the on/off time (e.g., Table 2 and Table 3) affects what the temperature is, the pressure that is being applied, and how the pulsing feels to the user.

Within the "on-times" for the slow pulse profile and the fast pulse profile, the Nitinol wires (e.g., Nitinol wires 245) can be pulsed with the following on/off times in Table 3.

TABLE 3

| | Profile | | | |
|---|---|---|---|---|
| | Slow Pulse | | Fast Pulse | |
| Size | On (milliseconds) | Off (milliseconds) | On (milliseconds) | Off (milliseconds) |
| Small | 30 | 30 | 25 | 5 |
| Med | 40 | 25 | 25 | 5 |
| Large | 60 | 25 | 25 | 5 |
| XLarge | 115 | 25 | 50 | 5 |

In S605, pulse width modulation (PWM) information can be received. The PWM information can be received in response to selection of a compression profile. For a size small active compression device 100, if the user selects (e.g., via the interface 300) the full contraction compression profile, the received PWM is 95. The PWM information can be based on a size of the active compression device 100, which is based on the size of the Nitinol wire (e.g., length and/or diameter). With reference to Table 2, each of sizes small, medium, large, and extra-large has a predetermined PWM for each compression profile and each heat setting for each compression profile. The different values in Table 2 for each size of the active compression device 100 can be stored locally in the controller 210 such that when the active compression device 100 receives the PWM information, the PWM information is already based on a known size of the active compression device 100.

In S610, a heat setting selection can be received. Referring to Table 2, each compression profile (e.g., full contraction, slow pulse, and fast pulse) can include a low and a high heat setting. The heat setting can be based on the "off" time. In the full contraction compression, the low heat setting has an "off" time of 14 seconds and the high heat setting has an "off" time of 11 seconds. The "off" time of 14 seconds may allow the Nitinol wire to fully cool off before being energized again. If 14 seconds corresponds to the minimum time it takes for the Nitinol wire to fully cool off, then energizing the Nitinol wire again after 11 seconds of "off" time can take advantage of the residual heat because the Nitinol wire has not had enough time to fully cool off. As a result, the high heat setting can be implemented by choosing an "off" time that does not allow the Nitinol wire to fully cool off. Additionally, the heat setting selection can be received in response to the user selecting the heat setting via the interface 300. After receiving the PWM information in S605 and the heat selection setting in S610, the process can continue to implement the selected compression profile by repeatedly energizing and subsequently turning off the Nitinol wires 245 in a predetermined pattern in S615, S620, S625, and S630.

For ease of understanding, the following descriptions for S615, S620, S625, and S630 will be in reference to Table 2 for the small sized active compression device for the full contraction profile on the high heat setting. However, it should be appreciated that the description is exemplary and that each sized active compression device has a PWM, "on" time, and "of" time for each heat setting selection in each compression profile.

In S615, a first wire (e.g., a first of the Nitinol wires 245) can be energized for a first predetermined amount of time. For the small sized active compression device 100 having received a PWM corresponding to the full contraction compression profile and the high heat setting selection, the first wire can be energized (e.g., "on") for 2.5 seconds. After the first wire has been energized (e.g., providing a predetermined amount of power to the wire) for the first predetermined amount of time, the first wire can be turned off for a second predeterminedamount of time in S620.

In S620, the first wire can be turned off for a second predetermined amount of time. The first wire can be turned off for 11 seconds for the high heat setting for the full contraction compression profile for the small sized active compression device 100. After the first wire has been "off" for 11 seconds, a second wire can be energized for a second predetermined amount of time in S625.

In S625, the second wire (e.g., a second of the Nitinol wires 245) can be energized for the first predetermined amount of time. The "on" time (e.g., 2.5 seconds) is the same as described in S615, but applied to the second wire. After the second wire has been energized for the first predetermined amount of time, the second wire can be turned off for the second predetermined amount of time in S630.

In S630, the second wire can be turned off for the second predetermined amount of time. The "off" time (e.g., 11 seconds) is the same as described in S620, but applied to the second wire.

In other words, S615, S620, S625, and S630, correspond to a pattern including turning the first wire on then off, turning the second wire on then off, and repeating the pattern until the device is entirely turned off or the device settings change.

In S635, it can be determined if any settings for the active compression device 100 have been changed. A user may change the heat setting and/or the compression profile selection. If no settings have changed, the process can return to S615 to continue energizing and turning off the first and second wires in the predetermined pattern. However, if any of the settings have changed in S635, the process can end, effectively starting again at S605 receiving the updated PWM information for a new compression profile and/or a new heat setting for the selected compression profile.

Figure 7:
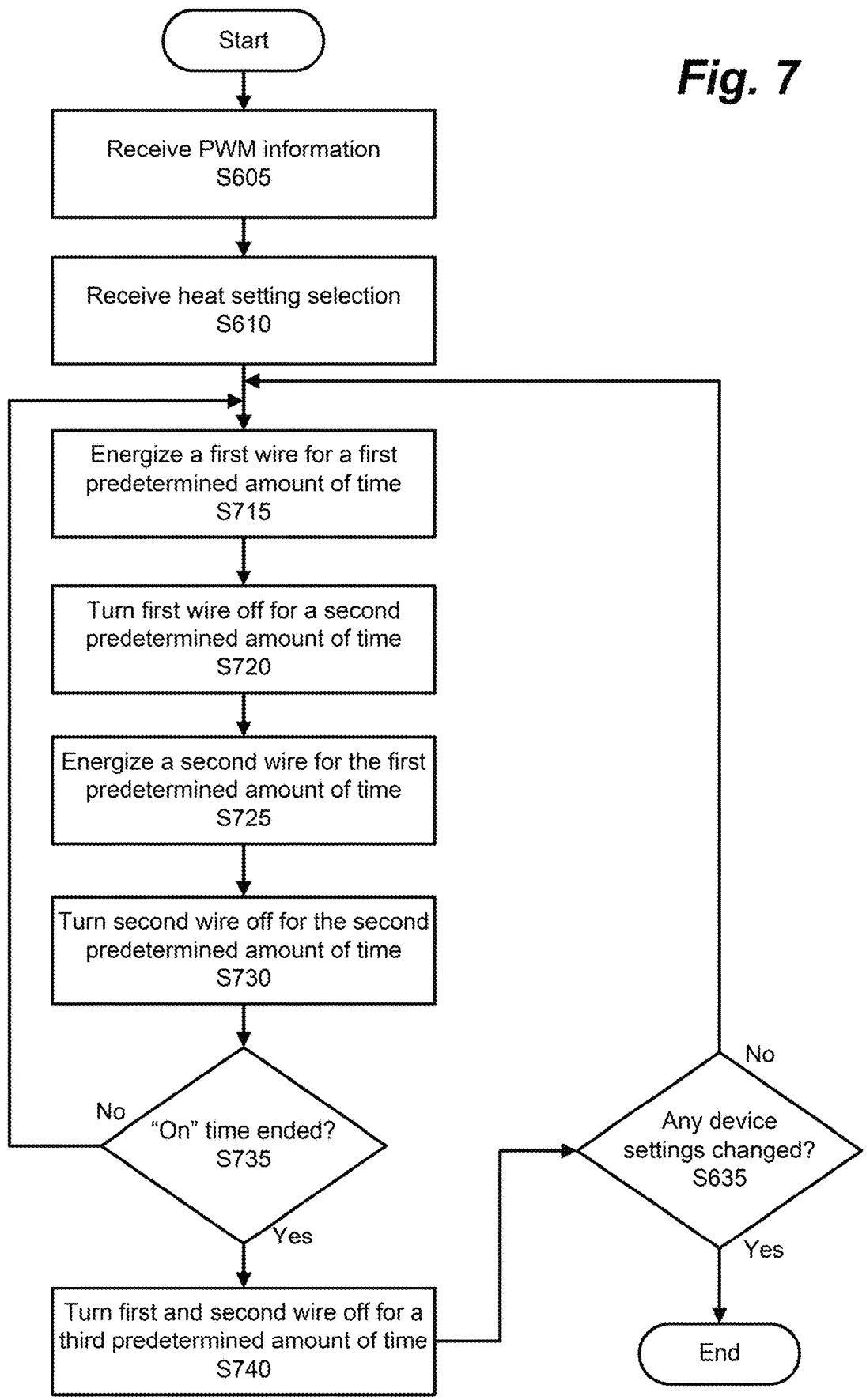
FIG. 7 is an algorithmic flow chart of a method for implementing a predetermined pulse pattern in a predetermined compression profile according to one or more aspects of the disclosed subject matter.

FIG. 7 is an algorithmic flow chart of a method for implementing a predetermined pulse pattern in a predetermined compression profile according to one or more aspects of the disclosed subject matter. In the slow pulse and fast pulse compression profiles, a predetermined pulse pattern can be implemented during the "on" time. For ease of understanding, description of FIG. 7 will be in reference to Table 2 for a medium sized active compression device 100 for the slow pulse contraction profile on the high heat setting. Additionally, S605, S610, and S635 can generally be understood as they are described in FIG. 6, but applying the slow pulse compression profile with the high heat setting to the medium sized active compression device 100.

S715, S720, S725, and S730 describe the pulse pattern implemented during the "on" time in Table 2. The pulse pattern during the "on" time can be based on Table 3.

In S715, a first wire (e.g., a first of the Nitinol wires 245) can be energized for a first predetermined amount of time. The pulse "on" time for the medium sized active compression device 100 for the slow pulse compression profile with the high heat setting selected is 40 milliseconds. After the first wire has been energized for the first predetermined pulse "on" time, the first wire can be turned off for a second predetermined amount of time in S720.

In S720, the first wire can be turned off for the second predetermined amount of time. The pulse "off" time for the medium sized active compression device 100 for the slow pulse compression profile with the high heat setting selected is 25 milliseconds. It should be appreciated that the "on" time and "off" time can be the same for the high heat and low heat settings. After the first wire is turned off for the second predetermined amount of time, a second wire can be energized for the first predetermined amount of time in S725.

In S725, the second wire (e.g., a second of the Nitinol wires 245) can be energized for the first predetermined amount of time. The pulse "on" time (e.g., 40 milliseconds) is the same as described in S715, but applied to the second wire. After the second wire has been energized for the first predetermined amount of time, the second wire can be turned off for the second predetermined amount of time in S730.

In S730, the second wire can be turned off for the second predetermined amount of time. The pulse "off" time (e.g., 25 milliseconds) is the same as described in S720, but applied to the second wire, After the second wire has been turned off for the second predetermined amount of time, it can be determined if the "on" time of the compression profile has ended in S735.

In S735, it can be determined if the "on" time for the compression profile has ended. Because the pulse "on" and pulse "off" times are occurring during the "on" time of the compression profile (e.g., 3 seconds for the medium sized active compression device implementing the slow pulse compression profile with the high heat setting), the pulse "on" times and pulse "off" times end when the "on" time for the compression profile ends. If it is determined that the "on" time of the compression profile (e.g., 3 seconds) has not ended, the processes can return to S715 to continue implementing the predetermined pattern described in S715, S720, S725, and S730. However, if it is determined that the "on" time for the compression profile has ended, the first and/or second wire can be turned off for a third predetermined amount of time in S740.

In S740, the first and/or second wire can be turned off for the third predetermined amount of time. The third predetermined amount of time can be the "off" time in the compression profile. The "off" time for the medium sized active compression device 100 for the slow pulse compression profile with the high heat setting can be 13 seconds. In other words, the pulse "on" (e.g., 40 milliseconds) and pulse "off" (e.g., 25 milliseconds) pattern can occur during the "on" time of the compression profile (e.g., 3 seconds), and when the "on" time of the compression profile ends, the pulse "on" and pulse "off" pattern also ends while the "off" time for the compression profile (e.g., 13 seconds) occurs. After the "off" time for the compression profile ends after the third predetermined amount of time, it can be determined if any device settings on the active compression device 100 have been changed as described in S635. If no device settings have been changed, the process can return to S715 to continue implementing the compression profile pattern including the pulse "on" pulse "off" pattern within the "on" time of the compression profile.

In the above description of FIG. 6 and FIG. 7, any processes, descriptions or blocks in flowcharts can be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art. The various elements, features, and processes described herein may be used independently of one another, or may be combined in various ways. All possible combinations and sub-combinations are intended to fall within the scope of this disclosure.

Additionally, it should be appreciated that the active compression device 100 is not limited to the compression profiles described herein. The active compression device 100 can be configured to implement any compression profiles within the physical limits of the Nitinol wires by applying current to the wires in any predetermined sequence/pattern that yields the desired compression profile.

Figure 8:
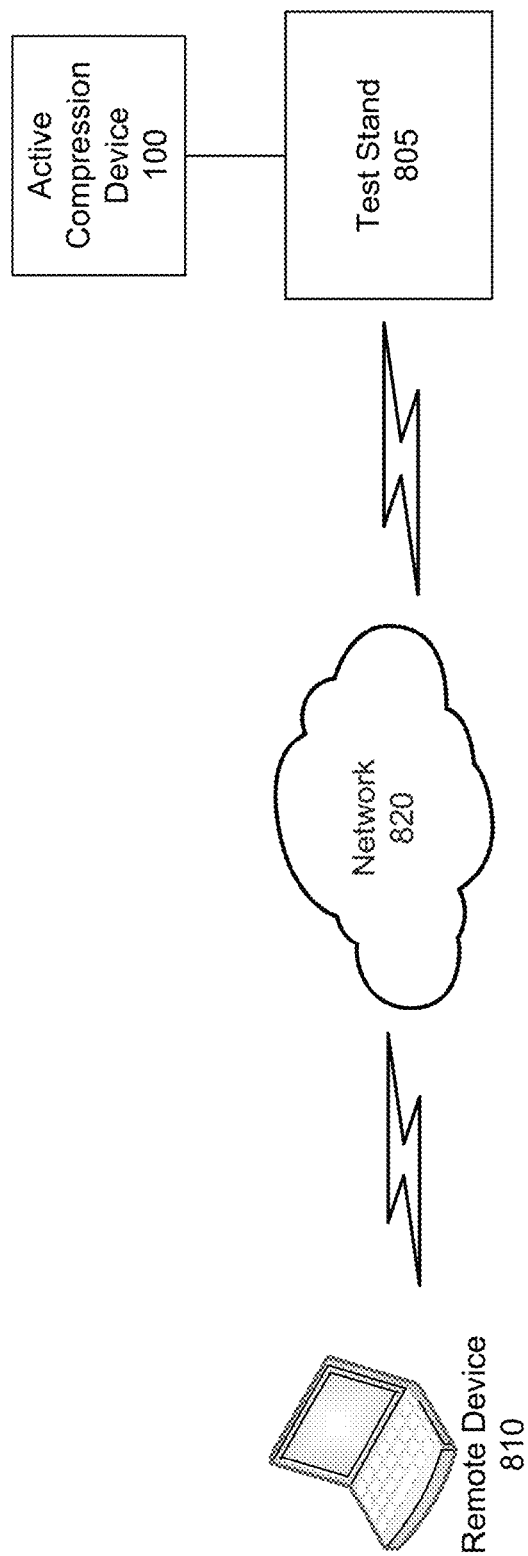
FIG. 8 is an exemplary overview of an active compression device test stand system according to one or more aspects of the disclosed subject matter.

FIG. 8 is an exemplary overview of an active compression device test stand system 800 (herein referred to as test stand system 800) according to one or more aspects of the disclosed subject matter. Previously, compression testing systems were developed to attempt to measure the force being applied from a compression stocking. The Medical Stocking Tester (MST) MK-V system uses a measuring probe that can be affixed to a human leg or a model (e.g., wooden) leg. A series of pressure sensors are positioned on a bladder, and as the bladder is inflated to specific pressures, each sensor records the force being applied at each sensor location. The components of the MST MK-V system include a calibration unit, probes, a leg (human or wooden model), the MST MK-V measuring device, and a computer running predetermined software corresponding to the system. However, comparison of in vivo (human leg) and in vitro (wooden leg) pressure measurements show discrepancies in accuracy of the measurements. Another method for testing compression comes from the Hosiery and Allied Trades Research Association (HATRA) in developing the HATRA pressure tester. The HATRA pressure tester consists of two main parts includes a garment former and a measuring head. A compression stocking is loaded onto the adjustable garment former, which simulates wearing of the garment on a human leg. Then the measuring head, pressed against the stretched fabric at various points along the length of the leg, displays a value for circumferential tension in the fabric. The value for circumferential tension in the fabric is converted to a value for pressure.

The test stand system 800 can include an active compression device test stand 805 (herein referred to as test stand 805) and a remote device 810 communicably coupled via a network 820. Additionally, a wearable compression device (e.g., the active compression device 100) can be positioned on the test stand 805 such that the test stand 805 can measure the force exerted by the active compression device 100.

The network 820 can represent one or more networks connecting the test stand 805 and the remote device 810. The network 820 can be a public network, such as the Internet, or a private network such as a local area network (LAN) or a wide area network (WAN) network, or any combination thereof and can also include a public switched telephone network (PSTN) or integrated services for digital network (ISDN) sub-networks. The network 820 can also be wired, such as an Ethernet network or a USB port, or can be wireless such as a cellular network including EDGE, 3G 4G, and LTE/LTE-A wireless cellular systems. The wireless network can also be Wi-Fi, Bluetooth, or any other wireless form of communication that is known.

Figure 9:
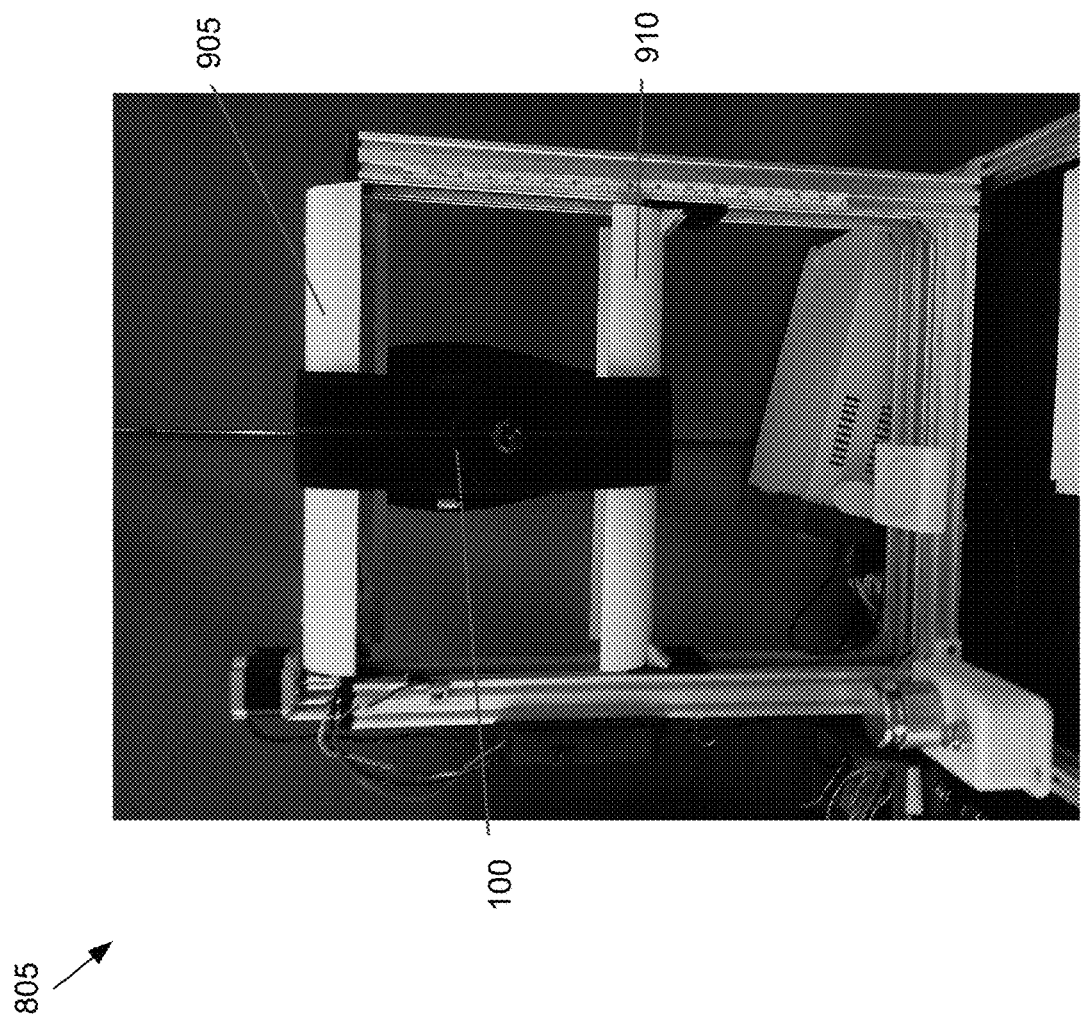
FIG. 9 is an exemplary active compression device test stand according to one or more aspects of the disclosed subject matter.

The test stand 805, as depicted in FIG. 9, can accommodate various sizes of devices ranging from extra-small to extra-large, wherein the sizes can be based on the length of the Nitinol wires 245. The test stand 805 can interface with custom software running on a remote device 105. The remote device 105 can be a laptop, computer, server, tablet, smartphone, PDA, and the like. The remote device 810 can send commands to the test stand 805 corresponding to instructions for implementing predetermined compression profiles. In response to the active compression device 100 exerting a force while positioned on the test stand 805, the remote device 810 can receive pressure data from the test stand 805, graph the forces measured, and display real-time pressure, peak pressure, pretension pressure, a difference between real-time pressure and pretension pressure, and the like. A stepper motor can be connected to a pretension frame through a linear screw which can adjust the distance between two frames of the test stand 805 to accommodate various sizes of active compression devices, as well as adjust the pretension when testing the active compression device 100. The two frames of the test stand 805 can include a stationary load cell frame 905 and a pretension frame 910. The pretension frame 910 can maintain a specified pretension force on the device using a closed-loop algorithm.

The closed loop algorithm for maintaining the specified pretension force using the pretension frame 910 can include a first step of determining if the pretension force subtracted from the real-time force (e.g., line 415 from FIG. 4A) is less than zero pounds of force. If the pretension force subtracted from the real-time force is less than zero pounds of force, the position of the pretension frame 910 can be incremented to change the distance between the pretension frame 910 and the stationary load cell 910. In other words, the pretension force can be increased. The incrementing of the position of the pretension frame 910 can be repeated until the pretension force subtracted from the real-time force is greater than or equal to zero pounds of force.

The test stand 805 and the active compression device 100 can work in concert in the test stand system 800 to reveal the effect of the power being applied to the Nitinol wires 245 in the active compression device 100. The test stand 805 allows for a visual representation of the forces implemented by the active compression device 100, which can provide a platform for precisely manipulating the amount of power applied to the Nitinol wires and the amount of time the power is applied and not applied (i.e., on and off times) to develop optimized predetermined compression profiles.

In other words, the test stand system 800 can provide specific calibration in the development and optimization of a predetermined compression profile. Many factors are considered including the power provided to the Nitinol wires, the subsequent heating of the Nitinol wires, how long to provide power, the pattern of providing power (on time) and not providing power (off time), the cooling of the Nitinol wires, whether or not the Nitinol wires are fully cooling, whether or not the Nitinol wires are purposely not allowed to fully cool based on a predetermined pattern, and the like.

Therefore, the test stand system 800 allows for the calibration, and subsequent optimization, of these considerations when developing a predetermined compression profile.

Figure 10:
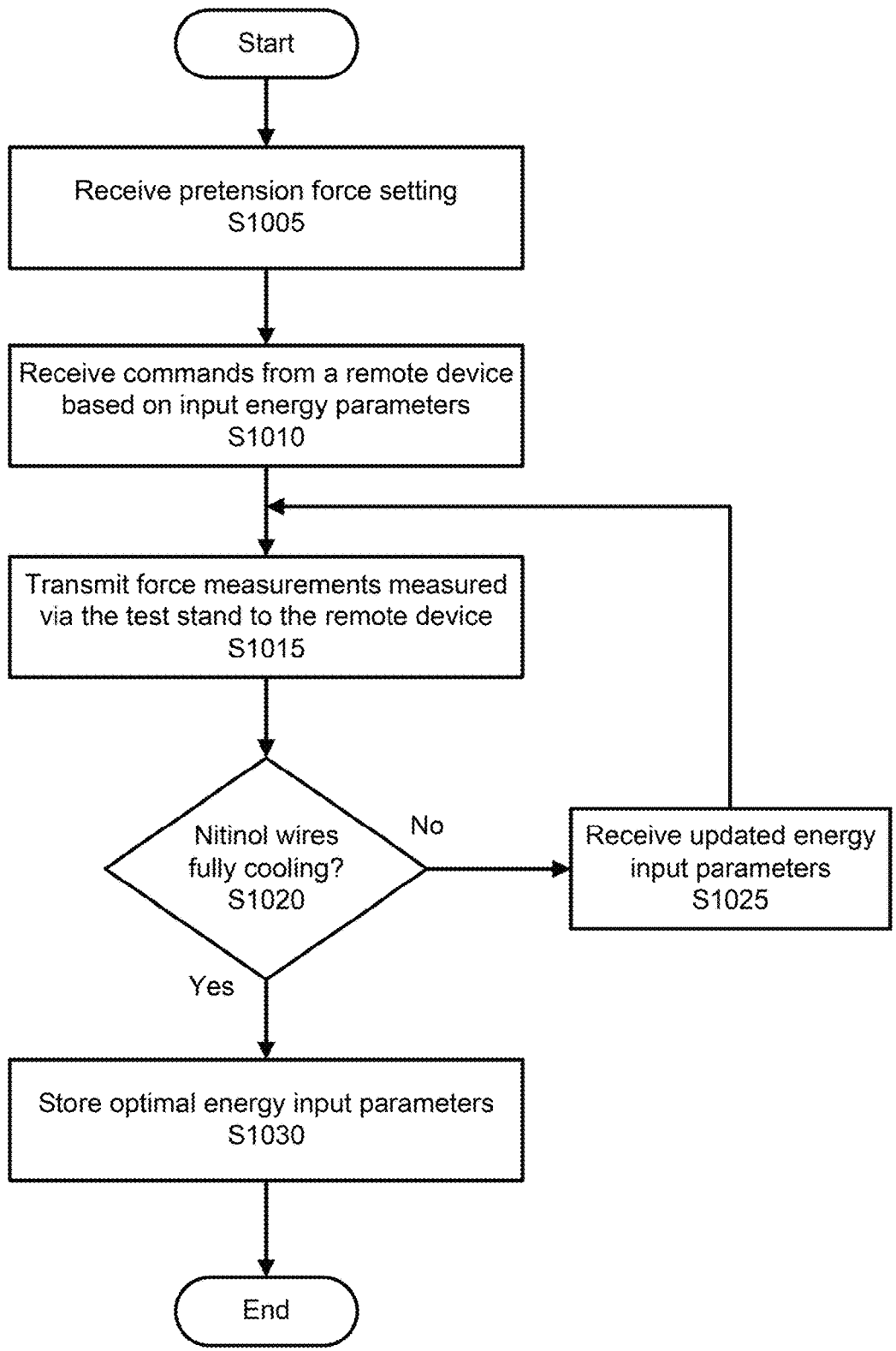
FIG. 10 is an algorithmic flow chart of a method for measuring a force exerted by an active compression device according to one or more aspects of the disclosed subject matter.

FIG. 10 is an algorithmic flow chart of a method for measuring a force exerted by the active compression device 100 according to one or more aspects of the disclosed subject matter. The force exerted by the active compression device 100 can be measured via the test stand 805.

in S1005, a pretension force setting can be received. The pretension force setting can correspond to a baseline force that the active compression device 100 may receive from the Boa lace 115 being manipulated by the Boa dial 120. The position and attachment of the active compression device 100 to the test stand 805 can mimic the active compression device 100 being worn by a user, for example.

In S1010, commands from a remote device (e.g., the remote device 810) based on input energy parameters can be received. The commands can be instructions corresponding to implementing a compression profile with specific PWM values, on and off times, and/or pulse on and pulse off time (e.g., as described with reference to Table 2 and Table 3).

In S1015, force measurements corresponding to the results of the compression profile tests (e.g., force measured by the test stand 805) can be transmitted to the remote device 810. The force measurements transmitted to the remote device 810 can be displayed in graphical form as seen in FIGS. 4A-4C and FIGS. 5A-5C. Upon analyzing the results based on the force measurements transmitted in S1010, it can be determined if the Nitinol wires (e.g., Nitinol wires 245) are fully cooling in S1020.

In S1020, it can be determined it the Nitinol wires 245 are fully cooling. If the real-time force does not intersect the pretension value (e.g., the pretension force setting in S1005), then the Nitinol wires 245 are not fully cooling.

If it is determined that the Nitinol wires 245 are not fully cooling, then updated energy input parameters can be received (e.g., as input via the interface seen in FIGS. 4A-4C and FIGS. 5A-5C displayed via the remote device 810) in S1025. Once the updated energy input parameters have been received in S1025, the process can return to S1015 to measure the force exerted by the active compression device 100 and transmit the force measurements to the remote device 805.

However, if it is determined that the Nitinol wires 245 are fully cooling, then optimal energy input parameters can be stored in local memory of the active compression device 100, in S1030. After optimal energy input parameters are stored in S1030, the process can end.

In the above description of FIG. 10, any processes, descriptions or blocks in flowcharts can be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art. The various elements, features, and processes described herein may be used independently of one another, or may be combined in various ways. All possible combinations and sub-combinations are intended to fall within the scope of this disclosure.

Figure 11:
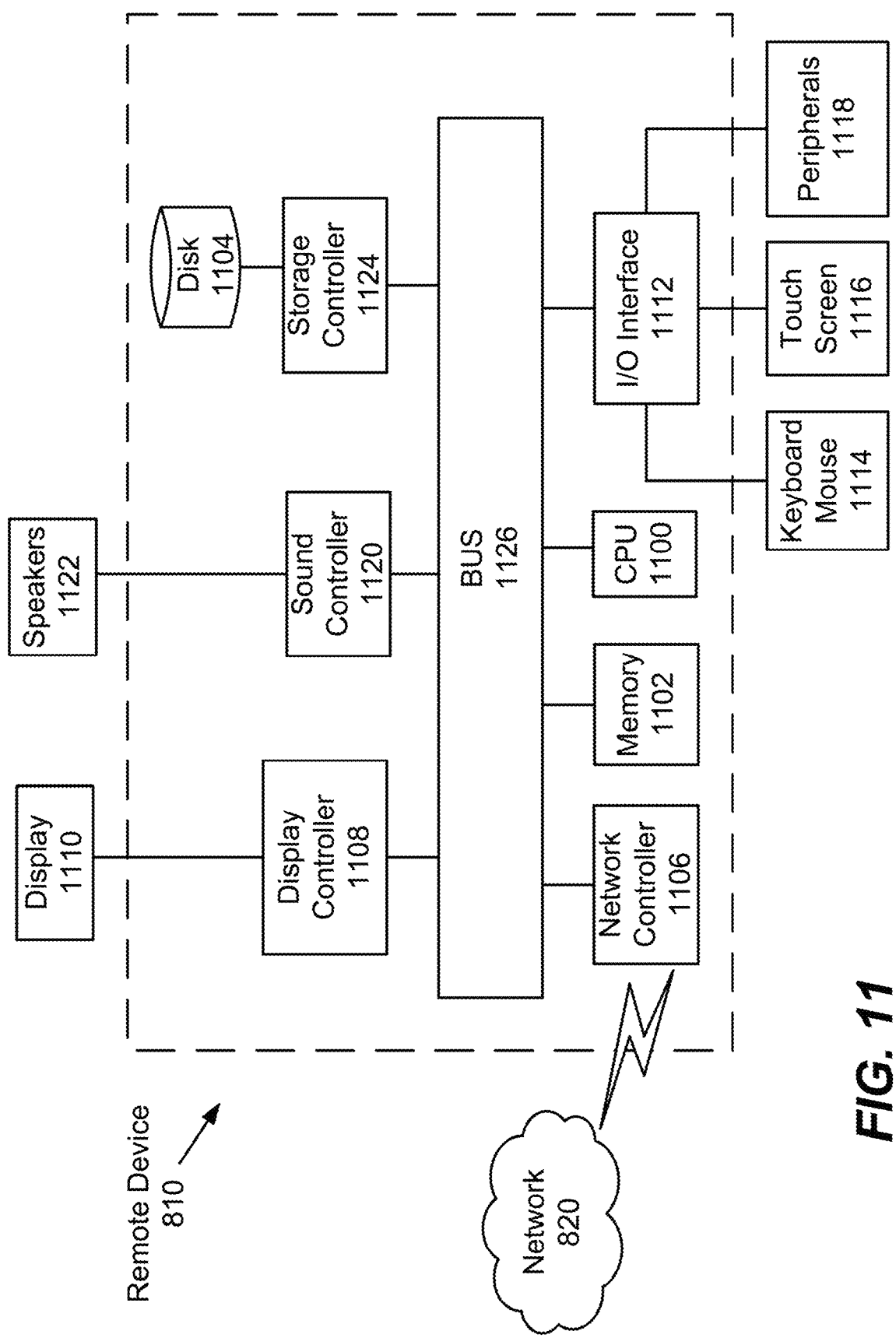
FIG. 11 is an exemplary hardware block diagram of a remote device according to one or more aspects of the disclosed subject matter.

Next, a hardware description of a computer/device (such as the remote device 810) according to exemplary embodiments is described with reference to FIG. 11. The hardware description described herein can also be a hardware description of the processing circuitry. In FIG. 11, the remote device 810 includes a CPU 1100 which performs one or more of the processes described above/below. The process data and instructions may be stored in memory 1102. These processes and instructions may also be stored on a storage medium disk 1104 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the remote device 810 communicates, such as a server or computer.

Further, the claimed advancements may be provided as a utility application, background daemon, or component of an operating system, or combination thereof, executing in conjunction with CPU 1100 and an operating system such as Microsoft Windows, UNIX, Solaris, LINUX, Apple MAC-OS and other systems known to those skilled in the art.

The hardware elements in order to achieve the remote device 810 may be realized by various circuitry elements. Further, each of the functions of the above described embodiments may be implemented by circuitry, which includes one or more processing circuits. A processing circuit includes a particularly programmed processor, for example, processor (CPU) 1100, as shown in FIG. 11. A processing circuit also includes devices such as an application specific integrated circuit (ASIC) and conventional circuit components arranged to perform the recited functions.

In FIG. 11, the remote device 810 includes a CPU 1100 which performs the processes described above. The remote device 810 may be a general-purpose computer or a particular, special-purpose machine. In one embodiment, the remote device 810 becomes a particular, special-purpose machine when the processor 1100 is programmed to measure a force exerted by the active compression device 100 (and in particular, any of the processes discussed with reference to FIG. 10).

Alternatively, or additionally, the CPU 1100 may be implemented on an FPGA, ASIC, PLD or using discrete logic circuits, as one of ordinary skill in the art would recognize. Further, CPU 1100 may be implemented as multiple processors cooperatively working in parallel to perform the instructions of the inventive processes described above.

The remote device 810 in FIG. 11 also includes a network controller 1106, such as an Intel Ethernet. PRO network interface card from Intel Corporation of America, for interfacing with network 250. As can be appreciated, the network 250 can be a public network, such as the Internet, or a private network such as an LAN or WAN network, or any combination thereof and can also include PSTN or ISDN sub-networks. The network 250 can also be wired, such as an Ethernet network, or can be wireless such as a cellular network including EDGE, 3G and 4G wireless cellular systems. The wireless network can also be WiFi, Bluetooth, or any other wireless form of communication that is known.

The remote device 810 further includes a display controller 1108, such as a graphics card or graphics adaptor for interfacing with display 1110, such as a monitor. A general purpose I/O interface 1112 interfaces with a keyboard and/or mouse 1114 as well as a touch screen panel 1116 on or separate from display 1110. General purpose I/O interface also connects to a variety of peripherals 1118 including printers and scanners.

A sound controller 1120 is also provided in the remote device 810 to interface with speakers/microphone 1122 thereby providing sounds and/or music.

The general purpose storage controller 1124 connects the storage medium disk 1104 with communication bus 1126, which may be an ISA, EISA, VESA, PCI, or similar, for interconnecting all of the components of the remote device 810. A description of the general features and functionality of the display 1110, keyboard and/or mouse 1114, as well as the display controller 1108, storage controller 1124, network controller 1106, sound controller 1120, and general purpose I/O interface 1112 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

The functions and features described herein may also be executed by various distributed components of a system. For example, one or more processors may execute these system functions, wherein the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a IAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

Having now described embodiments of the disclosed subject matter, it should be apparent to those skilled in the art that the foregoing is merely illustrative and not limiting, having been presented by way of example only. Thus, although particular configurations have been discussed herein, other configurations can also be employed. Numerous modifications and other embodiments (e.g., combinations, rearrangements, etc.) are enabled by the present disclosure and are within the scope of one of ordinary skill in the art and are contemplated as falling within the scope of the disclosed subject matter and any equivalents thereto. Features of the disclosed embodiments can be combined, rearranged, omitted, etc., within the scope of the invention to produce additional embodiments. Furthermore, certain features may sometimes be used to advantage without a corresponding use of other features. Accordingly, Applicant(s) intend(s) to embrace all such alternatives, modifications, equivalents, and variations that are within the spirit and scope of the disclosed subject matter.

The invention claimed is:

1. An active compression device, comprising:
   a controller assembly, wherein the controller assembly includes processing circuitry and is configured to:
   perform a predetermined push and hold compression profile in which a force applied by the compression device on a person wearing the device is held at a peak force, and
   actuate two or more shape memory wires integrated into the active compression device to apply a predetermined pattern of compressions corresponding to the predetermined push and hold compression profile in response to receiving a selection of the predetermined push and hold compression profile, wherein;
   during an on time of the push and hold compression profile in which the force is held at the peak force for approximately two seconds,
   provide, during said on time, a predetermined amount of power to a first shape memory wire for a first predetermined amount of time,
   turn off, during said on time, the first shape memory wire for a second predetermined amount of time when the first predetermined amount of time ends,
   provide, during said on time, the predetermined amount of power to a second shape memory wire for the first predetermined amount of time when the second predetermined amount of time ends, and
   turn off, during said on time, the second shape memory wire for the second predetermined amount of time when the first predetermined amount of time ends,
   thereby increasing the lifetime of the two or more memory wires.

2. The active compression device of claim 1, wherein the first predetermined amount of time and the second predetermined amount of time are determined based on one or more of the selected predetermined push and hold compression profile and a heat setting election.

3. The active compression device of claim 2, wherein the processing circuitry is further configured to
   receive the heat setting selection,
   set the second predetermine time to allow the first and second wires in the controller assembly to fully cool in response to the heat setting selection being a low heat setting, and
   set the second predetermined time to be less than the time to allow the first and second wires in the controller assembly to fully cool in response to the heat setting selection being a high heat setting.

4. The active compression device of claim 1, wherein the first shape memory wire and the second shape memory wire are Nitinol wires, wherein Nitinol wires contract to provide a predetermined amount of force in response to receiving the predetermined amount of power.

5. The active compression device of claim 1, wherein the predetermined amount of power provided to the first shape memory wire and the second shape memory wire is based on pulse width modulation (PWM), wherein a predetermined PWM corresponds to a predetermined length of the first and second wires in the controller assembly.

6. The active compression device of claim 1, wherein during the first predetermined amount of time, the processing circuitry is configured to
   provide power to the first wire for a third predetermined amount of time,
   turn off the first wire for a fourth predetermined amount of time,
   provide power to the second wire for the third predetermined amount of time, and
   turn off the second wire for the fourth predetermined amount of time.

7. An active compression device, comprising:
   a textile wrap configured to be secured around a waist of a user; and
   a controller assembly disposed within the textile wrap, wherein the controller assembly includes;

two or more shape memory wires configured to apply compression to the user's back in response to actuation of the two or more shape memory wires, and processing circuitry, the controller assembly configured to;

perform a predetermined push and hold compression profile in which a force applied by the compression device on a person wearing the device is held at a peak force, and activate a predetermined pattern of compressions corresponding to the predetermined push and hold compression profile in response to receiving a selection of the predetermined push and hold compression profile, wherein, during an on time of the push and hold compression profile in which the force is held at the peak force for approximately two seconds, provide, during said on time, a predetermined amount of power to a first shape memory wire for a first predetermined amount of time, turn off, during said on time, the first shape memory wire for a second predetermined amount of time when the first predetermined amount of time ends, provide, during said on time, the predetermined amount of power to a second shape memory wire for the first predetermined amount of time when the second predetermined time ends, and turn off, during said on time, the second shape memory wire for the second predetermined amount of time when the first predetermined amount of time ends, thereby increasing the lifetime of the two or more memory wires.

8. The active compression device of claim 7, wherein the active compression device includes a pre-tensioning device configured to apply an initial tension to one or more wires in the controller assembly.

9. The active compression device of claim 7, wherein the first predetermined amount of time and the second predetermined amount of time are determined based on the selected predetermined push and hold compression profile and a heat setting selection.

10. The active compression device of claim 9, wherein the processing circuitry is further configured to receive the heat setting selection, set the second predetermine time to allow the first and second shape memory wires to fully cool in response to the heat setting selection being a low heat setting, and set the second predetermined time to be less than the time to allow the first and second shape memory wires to fully cool in response to the heat setting selection being a high heat setting.

11. The active compression device of claim 9, wherein the actuation of the one or more shape memory wires corresponds to providing the predetermined amount of power to the first and second shape memory wires, wherein the first and second shape memory wires are Nitinol wires.

12. The active compression device of claim 9, wherein the redetermined amount of power provided to the first and second shape memory wires is based on pulse width modulation (PWM), wherein a predetermined PWM corresponds to a predetermined length of the first and second shape memory wires.

13. The active compression device of claim 9, wherein during the first predetermined amount of time, the processing circuitry is configured to provide power to the first shape memory wire for a third predetermined amount of time, turn off the first shape memory wire for a fourth predetermined amount of time, provide power to the second shape memory wire for the third predetermined amount of time, and turn off the second shape memory wire for the fourth predetermined amount of time.

14. A method for implementing a predetermined compression profile, comprising:

performing a predetermined push and hold compression profile for an active compression device in which a force applied by the compression device on a person wearing the device is held at a peak force; and actuating two or more shape memory wires integrated into the active compression device to apply a predetermined pattern of compressions corresponding to the predetermined push and hold compression profile in response to receiving a selection of the predetermined push and hold compression profile, wherein;

during an on time of the push and hold compression profile in which the force is held at the peak force for approximately two seconds, providing, during said on time, a predetermined amount of power to a first shape memory wire integrated into the active compression device for a first predetermined amount of time;

turning off, during said on time, the first shape memory wire for a second predetermined amount of time when the first predetermined amount of time ends;

providing, during said on time, the predetermined amount of power to a second shape memory wire integrated into the active compression device for the first predetermined amount of time when the second predetermined time ends; and turning off, during said on time, the second shape memory wire for the second predetermined amount of time when the first predetermined amount of time ends, thereby increasing the lifetime of the two or more memory wires.

15. The method of claim 14, wherein the first predetermined amount of time and the second predetermined amount of time are determined based on the selected predetermined push and hold compression profile and a heat setting selection.

16. The method of claim 15, wherein the processing circuitry is further configured to receive the heat setting selection;

set the second predetermine time to allow the first and second shape memory wires to fully cool in response to the heat setting selection being a low heat setting; and set the second predetermined time to be less than the time to allow the first and second shape memory wires to fully cool in response to the heat setting selection being a high heat setting.

17. The method of claim 15, wherein actuating the one or more shape memory wires corresponds to providing the predetermined amount of power to the first and second shape memory wires, wherein the first and second shape memory wires are Nitinol wires.

18. The method of claim 15, wherein the predetermined amount of power provided to the first and second shape memory wires is based on pulse width modulation (PWM), wherein a predetermined PWM corresponds to a predetermined length of the first and second shape memory wires.

19. The method of claim 15, wherein providing power during the first predetermined amount of time further comprises:

providing power to the first shape memory wire for a third predetermined amount of time;

turning off the first shape memory wire for a fourth predetermined amount of time; providing power to the second shape memory wire for the third predetermined amount of time; and turning off the second shape memory wire for the fourth predetermined amount of time.

20. The active compression device of claim 1, wherein in the case of the slow pulse compression profile during a slow pulse period of the compression profile of approximately six seconds, the force goes from no force to a force of about 5 pounds in the spiked pulse pattern, provide a predetermined amount of power to the first shape memory wire for a third predetermined amount of time that is different from the first predetermined amount of time, turn off the first shape memory wire for a fourth predetermined amount of time when the third predetermined amount of time ends, the fourth predetermined amount of time being different from the second predetermined amount of time, provide the predetermined amount of power to a second shape memory wire for the third predetermined amount of time when the fourth predetermined time ends, and turn off the second shape memory wire for the fourth predetermined amount of time when the third predetermined amount of time ends, thereby increasing the lifetime of the one or more memory wires.

* * * * *